(12) United States Patent
Johnson et al.

(10) Patent No.: US 9,365,893 B2
(45) Date of Patent: Jun. 14, 2016

(54) METHODS OF MAPPING POLYMORPHISMS AND POLYMORPHISM MICROARRAYS

(75) Inventors: Eric A. Johnson, Eugene, OR (US); Guowen Liu, Cary, NC (US); Michael R. Miller, Eugene, OR (US)

(73) Assignee: State of Oregon Acting by and through the State Board of Higher Education on behalf of the University of Oregon, Eugene, OR (US)

( * ) Notice: Subject to any disclaimer, the term of this patent is extended or adjusted under 35 U.S.C. 154(b) by 2567 days.

(21) Appl. No.: 11/914,099

(22) PCT Filed: May 10, 2006

(86) PCT No.: PCT/US2006/018150
§ 371 (c)(1),
(2), (4) Date: May 2, 2008

(87) PCT Pub. No.: WO2006/122215
PCT Pub. Date: Nov. 16, 2006

(65) Prior Publication Data
US 2008/0194418 A1  Aug. 14, 2008

Related U.S. Application Data

(60) Provisional application No. 60/782,424, filed on Mar. 14, 2006, provisional application No. 60/679,693, filed on May 10, 2005.

(51) Int. Cl.
*C12Q 1/68* (2006.01)
*C40B 20/04* (2006.01)
*C40B 30/04* (2006.01)

(52) U.S. Cl.
CPC ..................................... *C12Q 1/683* (2013.01)

(58) Field of Classification Search
None
See application file for complete search history.

(56) References Cited

U.S. PATENT DOCUMENTS

| | | | |
|---|---|---|---|
| 4,794,075 A | 12/1988 | Ford et al. | |
| 5,698,400 A | 12/1997 | Cotton et al. | |
| 5,723,320 A | 3/1998 | Dehlinger | |
| 5,726,022 A * | 3/1998 | Burmer | 435/6 |
| 5,728,524 A | 3/1998 | Sibson | |
| 5,750,335 A | 5/1998 | Gifford | |
| 5,922,535 A | 7/1999 | Huo | |
| 6,045,994 A | 4/2000 | Zabeau et al. | |
| 6,468,742 B2 | 10/2002 | Nerenberg | |
| 6,713,258 B2 | 3/2004 | Kilian | |
| 6,783,943 B2 | 8/2004 | Christian et al. | |
| 6,924,104 B2 | 8/2005 | Weissman et al. | |
| 7,026,115 B1 | 4/2006 | Zabeau et al. | |
| 7,135,284 B1 | 11/2006 | Behlke et al. | |
| 7,141,371 B2 | 11/2006 | Liu | |
| 7,166,429 B2 | 1/2007 | Van Eijk et al. | |
| 7,217,516 B2 | 5/2007 | Van Eijk et al. | |
| 7,378,245 B2 | 5/2008 | Liu | |
| 7,563,581 B2 | 7/2009 | Liu | |
| 2002/0042063 A1 | 4/2002 | Kilian | |
| 2002/0094116 A1 | 7/2002 | Frost et al. | |
| 2002/0146723 A1 | 10/2002 | Krontiris et al. | |
| 2003/0048934 A1* | 3/2003 | Benson | 382/129 |
| 2003/0186279 A1 | 10/2003 | Kennedy et al. | |
| 2004/0048257 A1* | 3/2004 | Liu | 435/6 |
| 2005/0032082 A1 | 2/2005 | Kilian | |
| 2005/0064406 A1* | 3/2005 | Zabarovsky et al. | 435/6 |
| 2005/0079510 A1 | 4/2005 | Berka et al. | |
| 2006/0029267 A1 | 2/2006 | Frost et al. | |

FOREIGN PATENT DOCUMENTS

| | | |
|---|---|---|
| EP | 1 362 929 | 11/2003 |
| WO | WO 99/23256 | 5/1999 |
| WO | WO 99/31272 | 6/1999 |
| WO | WO 00/34518 | 6/2000 |
| WO | WO 00/44936 | 8/2000 |
| WO | WO 00/50632 | 8/2000 |
| WO | WO 00/55364 | 9/2000 |
| WO | WO 02/083955 | 10/2002 |
| WO | WO02/086163 | * 10/2002 |
| WO | WO 2004/044225 | 5/2004 |
| WO | WO 2006/122215 | 11/2006 |
| WO | WO 2006/137733 | 12/2006 |
| WO | WO 2007/087291 | 8/2007 |
| WO | WO 2007/114693 | 10/2007 |

OTHER PUBLICATIONS

Ji et al. Science. vol. 293: 2266-2269; Sep. 21, 2001.*
Li et al., "NotI subtraction and NotI-specific microarrays to detect copy number and methylation changes in whole genomes," *PNAS* 99 (16): 10724-10729, 2002.
Bonetta, "Genome sequencing in the fast lane," *Nature Methods*, 3(2):141-147 (2006).
Buckley, "Development and Application of Microarray-Based Comparative Genomic Hybridization: Analysis of Neurofibromatosis Type-2, Schwannomatosis and Related Tumors," Abstract for Doctoral Thesis from Uppsala University, *Comprehensive Summaries of Uppsala Dissertations from the Faculty of Medicine* (2005).

(Continued)

*Primary Examiner* — Nancy J Leith
(74) *Attorney, Agent, or Firm* — Klarquist Sparkman, LLP

(57) ABSTRACT

Described are methods for the high-throughput discovery and genotyping of nucleotide polymorphisms in DNA, including single nucleotide polymorphism (SNPs) and short deletions and insertions. These methods take advantage of the fact that differences in DNA sequence result in the differential presence of restriction endonuclease digestion sites. Approaches involve isolation of short DNA fragments ("tags") near restriction endonuclease sites. The presence of one (or two) of these tags indicates that a site was present. Regions of DNA with a restriction site in only one individual create an opportunity for primer extension to produce labeled material, which can be assayed on a platform that employs a collection of nucleic acids. Efficient variant detection microarrays and bead libraries are provided that contain genomic tags with different representations between two populations, so that most elements in the collection of nucleic acids contain a SNP between populations of interest.

5 Claims, 4 Drawing Sheets

(56) References Cited

OTHER PUBLICATIONS

Chee et al., "Accessing Genetic Information with High-Density DNA Arrays," *Science*, 274(5287):610-614 (1996).
Cronn et al., "Multiplex sequencing of plant chloroplast genomes using Solexa sequencing-by-synthesis technology," *Nucleic Acids Research*, 36(19):e122 (2008).
Duffy, "GAL4 System in *Drosophila*: A Fly Geneticist's Swiss Army Knife," *Genesis*, 34:1-15 (2002).
Gotoh and Oishi, "Screening of Gene-Associated Polymorphisms by Use of In-Gel Competitive Reassociation and EST (cDNA) Array Hybridization," *Genome Research*, 13:492-495 (2003).
Hacia, "Resequencing and mutational analysis using oligonucleotide microarrays," *Nature Genetics Supplement*, 21:42-47 (1999).
Jaccoud et al., "Diversity Arrays: a solid state technology for sequence information independent genotyping," *Nucleic Acids Research*, 29 (4):e25 (2001).
Liu et al., "SNP selection for a microarray based high-throughput genotyping assay," Abstract for a poster presented at Jul. 31-Aug. 4, 2004, meeting—12$^{th}$ International Conference on Intelligent Systems for Molecular Biology (accessible on-line at the website iscb.org/ismb2004/posters/guoying_liuATaffymetrix.com_463.html).
Lucito et al., "Representational Oligonucleotide Microarray Analysis: A High-Resolution Method to Detect Genome Copy Number Variation," *Genome Research*, 13:2291-2305 (2003).
Martin et al., "A rapid method to map mutations in *Drosophila*," *Genome Biology*, 2(9):research0036.1-0036.12 (2001).
Melton, "On the trail of SNPs," *Nature*, 422:917-923 (2003).
Ramon et al., "Pyrosequencing: A one-step method for high resolution HLA typing," *Journal of Translational Medicine*, 1:9 (2003).
Schriefer et al., "Low pressure DNA shearing: a method for random DNA sequence analysis," *Nucleic Acids Research*, 18(24):7455-7456 (1990).
Wang et al., "Large-Scale Identification, Mapping, and Genotyping of Single-Nucleotide Polymorphisms in the Human Genome," *Science*, 280:1077-1082 (1998).
Zabarovska et al.,"*Not*1 passporting to identify species composition of complex microbial systems," *Nucleic Acids Research*, 31(2):e5 (2003).
Defilippes, "Restriction Enzyme Digests of Rapidly Renaturing Fragments of Vaccinia Virus DNA," *Journal of Virology*, vol. 17, No. 1, pp. 227-238, 1976.
Sambrook et al., "Bacteriophage λ and Its Vectors," *Molecular Cloning: A Laboratory Manual, Third Edition*, vol. 1, p. 2.110, 2001.
Arabidopsis restriction enzyme digest analysis, 1 page, received 2011.
Notice of Opposition and Opposition Brief, European Pat. App. No. 06752497.5, dated Nov. 2, 2011 (23 pages).

\* cited by examiner

1) Shear

2) Digest sheared fragments

3) Ligate linker and purify

4) Fluorescently label each pool of tags.

5) Competitively hybridize to microarray

1) Digest genomic DNA
2) Anneal cut genomic
3) Extend fluorescently-labeled DNA from mismatched fragments
4) Hybridize to microarray

A)
B)
C)
D)

Red
Red
Red

METHODS OF MAPPING POLYMORPHISMS AND POLYMORPHISM MICROARRAYS

CROSS REFERENCE TO RELATED APPLICATIONS

This is the U.S. National Stage of International Application No. PCT/US2006/018150, filed May 10, 2006, which was published in English under PCT Article 21(2), which in turn claims the benefit of U.S. Provisional Application No. 60/679,693, filed May 10, 2005, and U.S. Provisional Application No. 60/782,424, filed Mar. 14, 2006. All of these applications are incorporated herein in their entirety.

FIELD

This disclosure relates to methods, materials, and devices for detecting, resolving, and mapping polymorphisms and genetic differences. It relates to detection of large numbers of polymorphisms, including specifically single nucleotide and other short polymorphisms. Representative methods employ differential enzyme digestion and hybridization.

BACKGROUND OF THE DISCLOSURE

Genetic variation exists between different individuals of a species. For some organisms, a single nucleotide polymorphism (SNP) may occur every 100 basepairs, while other species may have rates greater than one change in 1000 (Sachidanandam et al., Nature 409(6822): 928-33, 2001). Small (short) nucleotide insertions and deletions may occur at similar frequencies. While such polymorphisms can complicate some forms of genetic analysis, they can also be harnessed to map the inheritance of chromosomal regions. In model organisms, SNPs have been used to map the location of mutations from genetic screens in recombinant progeny (Berger et al., Nat Genet. 29(4): 475-81, 2001; Martin et al., Genome Biol 2(9): RESEARCH 0036, E-pub Aug. 30, 2001; Wicks et al., Nat Genet. 28(2): 160-4, 2001; Stickney et al., Genome Res 12(12): 1929-34, 2002), and to identify the location of phenotypic modifiers in quantitative trait locus mapping (QTL). In humans, SNPs have been used to identify disease alleles and phenotypic modifiers in association studies (Bader, Pharmacogenomics 2(1): 11-24. 2001; Pharoah et al., Nat Rev Cancer 4(11): 850-60, 2004).

The power of using SNPs increases with the number of SNPs identified, and methods for genotyping individuals for the presence of particular SNPs have improved. In sequenced organisms, bioinformatic approaches of comparing expressed sequence tag (EST) data have yielded a wealth of potential SNPs (Marth et al., Nat Genet. 23(4): 452-6, 1999; Buetow et al., Proc Natl Acad Sci USA 98(2): 581-4, 2001; Hu et al., Pharmacogenomics J 2(4): 236-42, 2002). More recently, high-throughput approaches using high-density oligonucleotide arrays have been employed for SNP discovery (Matsuzaki et al., Genome Res 14(3): 414-25, 2004). However, these approaches can only be used to study organisms with a well-developed genomics infrastructure and prior knowledge of genome or EST sequence, at significant cost.

Likewise, high-resolution SNP maps have been generated by comparative genome sequencing of lab populations of interest, such as the common genetic screen lines FRT 82 and rucuca in Drosophila (Berger et al., Nat Genet 29(4): 475-81, 2001; Martin et al., Genome Biol 2(9): RESEARCH 0036, E-pub Aug. 30, 2001). These SNP maps are optimized for the lines tested, although some proportion of SNPs from the tested populations are expected to be present in other fly lines as well. The effort involved in creating these maps makes it unlikely that many additional lines of interest will have SNPs discovered at high density in the near future by comparative sequencing, despite the need for many lines of different genetic backgrounds for optimal isolation and recovery of mutations of interest.

A frequent objective of previous SNP discovery screens was to identify SNPs that disrupted restriction endonuclease recognition sites. Disruption of such a site allowed for low-cost and rapid genotyping of the potential SNP from different individuals, as the read-out was the differential digestion of the SNP region. More recently, the capture and sequencing of genomic regions around restriction sites has been used to sample genomes and determine areas of DNA duplication in cancer and microbial population dynamics (Wang et al., Proc Natl Acad Sci USA 99(25): 16156-61, 2002; Zabarovslca et al., Nucleic Acids Res 31(2): E5-5, 2003). In these approaches, SNPs have been confounding factors rather than the objective of the techniques, in that SNPs cause uncertainty in the assignment of the short sequence reads to their proper position in the genome. Other techniques have been used to distinguish the relatedness of individual organisms within a species (see, e.g., U.S. Pat. No. 5,713,258).

While the ability to detect nucleotide polymorphisms has improved rapidly, it is not routine to detect large number of polymorphisms between two individuals, particularly in organisms lacking thorough genomic and cDNA sequence information.

SUMMARY OF THE DISCLOSURE

Provided herein in various embodiments are new methods for the routine detection of polymorphisms (including SNPs and short deletions or insertions, and other variants), and the creation of new types of nucleic acid element collections (including microarrays and bead libraries) that optimize the detection of polymorphisms from these methods.

Methods described herein demonstrate the use of restriction site tags for single nucleotide polymorphism (SNP) discovery and mutation and variant mapping.

In one example method, fragments (tags) near restriction sites are isolated from genomic DNA. In a working embodiment, the fragments (tags) are about 1 kb in length. In individuals where nucleotide polymorphisms disrupt the restriction site, the associated tag will be absent from the restriction site tags selected (in that it will not be the expected size). Hybridization of labeled restriction site tags (also referred to as restriction site associated DNA, or RAD) from two different individuals to a collection of nucleic acid elements (for instance, in a microarray or a bead library) allows for polymorphism discovery at array elements with differential hybridization between the two individuals. Strategies for optimizing this protocol and using the resulting SNP information in mapping mutations are also described.

Yet further provided methods demonstrate the use of extension from mismatched restriction sites for polymorphism discovery and mapping.

In an example of such methods, restriction enzyme-digested genomic DNA from two individuals are mixed and annealed. If nucleotide polymorphisms disrupt a restriction site in one of the two individuals, then the site of polymorphism will create two short fragments (from one individual) bound to a longer, uncut fragment (from the other individual). One of the short fragments can be used as a primer for extension by DNA polymerase, allowing the incorporation of label (e.g., fluorescent dye-linked nucleotides) near the polymorphism site. Hybridization of the resultant labeled DNA to a collection of nucleic acids (e.g., in a microarray or bead library) allows for SNP discovery at nucleic acid elements with strong hybridization signal intensity. Strategies for optimizing this protocol and using the resulting SNP information in mapping mutations are also described.

Also described are restriction site tag collections, including for instance microarrays and bead libraries. These collections, arrays and libraries have particular utility for detecting polymorphism discovered, for instance, by the methods described herein.

It is acknowledged and recognized that the polymorphism detection and discovery methods described herein can be used with variety of platforms for the detection of polymorphisms (e.g., SNPs and small deletions or insertions) and generally for nucleic acid variations between two samples. For projects involving a large amount of SNP discovery or mapping, there are benefits to using a restriction site genomic tag array or bead library as described herein. A genomic tag array or bead library contains elements that consist of DNA flanking sites of digestion for a particular restriction enzyme in the genome. Thus, when the experimental and array restriction sites match, each element of the collection is capable of detecting a restriction site tag (in some embodiment methods), or an extension from restriction site polymorphism (in other embodiment methods). By way of example, such restriction site genomic tag arrays provided higher rates of SNP discovery and higher resolution mapping. Also described are subtracted restriction site genomic tag collections (e.g., arrays and bead libraries), wherein the array or library contains (substantially) only elements that differ between two individuals (or two reference samples). This is possible when the tags from the two individuals (or reference samples) undergo a round of subtractive hybridization, a procedure that removes DNA in common between the two samples. In such subtractive genomic tag arrays and libraries, each element could assay a polymorphism between individuals (or an individual and one or both reference samples).

An advantage of the techniques described herein is that it is possible to discover a large number of SNPs in the exact population of interest, using only the genomic DNA and a few restriction endonucleases. Thus, researchers need no longer be confined to working with genotypes where SNP maps have already been developed, or even to organisms with sequenced genomes.

The foregoing and other features and advantages will become more apparent from the following detailed description of several embodiments, which proceeds with reference to the accompanying figures.

BRIEF DESCRIPTION OF THE FIGURES

FIG. 3A: Experiments digesting the same genomic DNA with different restriction enzymes will identify different SNPs in the genome (mock array pictures). FIG. 3B: These SNPs can be combined to create a more detailed SNP map than would be possible using any single digestion (SNPs identified with different restriction enzymes are shown with thick and thin lines).

FIG. 4A: Hybridization of single recombinant lines versus rucuca line. Vertical lines indicate SNPs and FRT 82 chromosomal material. SNPs in common between the three recombinants suggest mutation is in that region (dashed box). FIG. 4B: Isolating tags from all three lines and hybridizing simultaneously versus rucuca line creates a gradient of intensity ratios, with the highest intensity in the common region (thick vertical bars).

FIG. 7A: Test plasmids were cut at common XhoI sites (lines) and the plasmid at right cut at a BamHI site (triangle). FIG. 7B: Annealing of plasmids expected to form a perfect match (left) and a mismatch of two shorter fragments onto a longer fragment (right). FIG. 7C: Fluorescently labeled nucleotides were incorporated and material hybridized to test array of larger XhoI fragment (columns 1, 3, and 5) and shorter fragment (columns 2, 4, and 6). Fluorescent material was only seen hybridizing to larger fragment spot. FIG. 7D: Test of protocol after annealing FRT 82 and rucuca genomes digested by BamHI. Red spots (indicated with arrows) are seen on genomic array at a rate similar to predictions.

SEQUENCE LISTING

Figure 1:
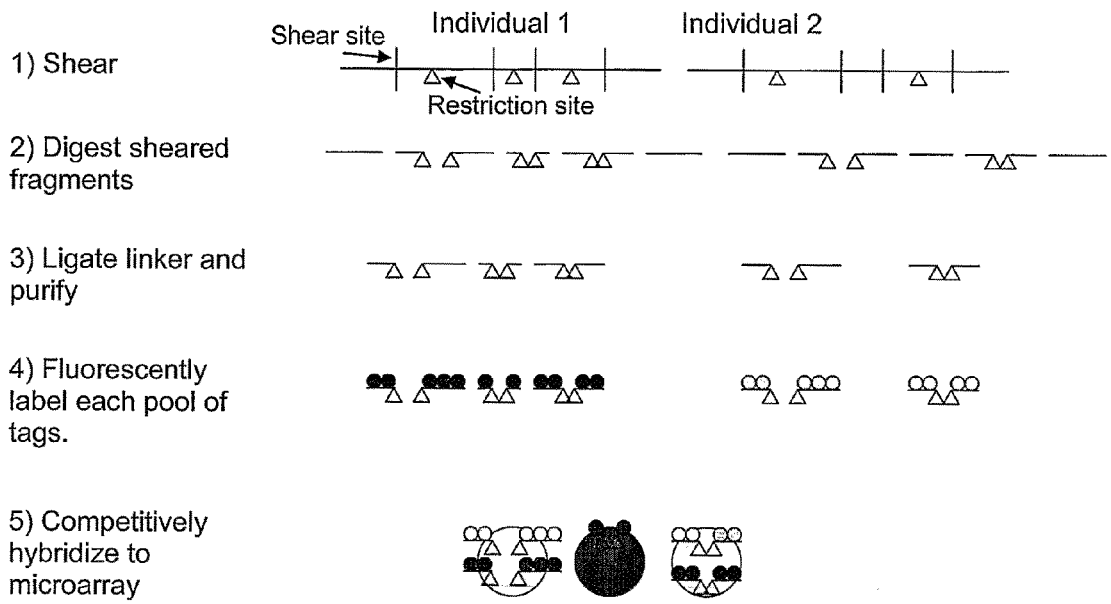
FIG. 1 is a schematic of a representative method for SNP detection by hybridization of restriction site tags to a microarray.

Any nucleic acid and amino acid sequences listed herein or in the accompanying sequence listing are shown using standard letter abbreviations for nucleotide bases, and three letter code for amino acids, as defined in 37 C.F.R. 1.822. In at least some cases, only one strand of each nucleic acid sequence is shown, but the complementary strand is understood as included by any reference to the displayed strand.

SEQ ID NOs: 1 and 2 are the nucleic acid sequences of synthetic oligonucleotides used to generate a representative biotin linker specific for an EcoRI digestion.

SEQ ID NOs: 3 and 4 are the nucleic acid sequences of oligonucleotides used to generate blunt-end linkers for use with random amplification.

DETAILED DESCRIPTION

I. Abbreviations cDNA: complementary DNA
DNA: deoxyribonucleic acid
EST: expressed sequence tag
GRIdS: genome-wide RFLP identification and segregation
PCR: polymerase chain reaction
RAD: restriction site associated DNA
RE: restriction enzyme (endonuclease)
RNA: ribonucleic acid
QTL: quantitative trait locus mapping
SNP: single nucleotide polymorphism
SNV: single nucleotide variant
ssRNA: single stranded RNA

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Addressable: Capable of being reliably and consistently located and identified, as in an addressable location on an array.

Array: An arrangement of molecules, particularly biological macromolecules (such as polypeptides or nucleic acids) in addressable locations on a substrate, usually a flat substrate such as a membrane, plate or slide. The array may be regular (arranged in uniform rows and columns, for instance) or irregular. The number of addressable locations on the array can vary, for example from a few (such as three) to more than 50, 100, 200, 500, 1000, 10,000, or more. A "microarray" is an array that is miniaturized to such an extent that it benefits from microscopic examination for evaluation.

Within an array, each arrayed molecule (e.g., polynucleotide or oligonucleotide) is addressable, in that its location can be reliably and consistently determined within the at least two dimensions, usually defined and on by the array surface. Thus, in ordered arrays the location of each molecule sample (feature, element) is usually assigned to the sample at the time when it is spotted onto or otherwise applied to the array surface, and a key may be provided in order to correlate each location with the appropriate feature. Often, ordered arrays are arranged in a symmetrical grid pattern, but samples could be arranged in other patterns (e.g., in radially distributed lines, spiral lines, or ordered clusters).

Arrays are usually computer readable, in that a computer can be programmed to correlate a particular address on the array with information (such as identification of the arrayed sample and hybridization or binding data, including for instance one or more signal intensity readings). In some examples of computer readable array formats, the individual spots on the array surface will be arranged regularly, for instance in a Cartesian grid pattern, that can be correlated to address information by a computer.

The sample application spot (or feature, or element) on an array may assume many different shapes. Thus, though the term "spot" may be used herein, it refers generally to a localized deposit of nucleic acid or other biomolecule, and is not limited to a round or substantially round region. For instance, substantially square regions of application can be used with arrays, as can be regions that are substantially rectangular (such as a slot blot-type application), triangular, oval, irregular, and so forth. The shape of the array substrate itself is also immaterial, though it is usually substantially flat and may be rectangular or square in general shape.

Binding or interaction: An association between two substances or molecules, such as the hybridization of one nucleic acid molecule to another (or itself). The disclosed oligonucleotide arrays are used to detect binding of a labeled nucleic acid molecule (target) to an immobilized nucleic acid molecule (probe) in one or more features of the array. A labeled nucleic acid molecule "binds" to a nucleic acid molecule in a spot on an array if, after incubation of the (labeled) target molecule (usually in solution or suspension) with or on the array for a period of time (usually 5 minutes or more, for instance 10 minutes, 20 minutes, 30 minutes, 60 minutes, 90 minutes, 120 minutes or more, for instance over night or even 24 hours), a detectable amount of that molecule associates with a nucleic acid feature of the array to such an extent that it is not removed by being washed with a relatively low stringency buffer (e.g., higher salt (such as 3×SSC or higher), room temperature washes). Washing can be carried out, for instance, at room temperature, but other temperatures (either higher or lower) also can be used.

Targets will bind probe nucleic acid molecules within different features on the array to different extents, based at least on sequence homology, and the term "bind" encompasses both relatively weak and relatively strong interactions. Thus, some binding will persist after the array is washed in a more stringent buffer (e.g., lower salt (such as about 0.5 to about 1.5×SSC), 55-65° C. washes).

Where the probe and target molecules are both nucleic acids, binding of the test or reference molecule to a feature on the array can be discussed in terms of the specific complementarity between the probe and the target nucleic acids.

cDNA: A DNA molecule lacking internal, non-coding segments (introns) and regulatory sequences which determine transcription. cDNA may be synthesized in the laboratory by reverse transcription from messenger RNA extracted from cells.

Cell sample: A sample of cells, either which may be homogenous or heterogeneous as to cell type, from which nuclei can be harvested. In particular examples, cell samples are taken from different primary cells; from embryonic stem cells; an immortalized cell line; a homologous primary cell sample; from a cell type at different stages of development; from different times in a disease progression; from infected and uninfected homologous cells; from cells (or cells from subjects) treated with different conditions (e.g., drugs, drug regimes, temperature or other grown characteristics, carbon sources or food supplies), and so forth.

DNA: DNA is a long chain polymer that contains the genetic material of most living organisms (the genes of some viruses are made of ribonucleic acid (RNA)). The repeating units in DNA polymers are four different nucleotides, each of which includes one of the four bases (adenine, guanine, cytosine and thymine) bound to a deoxyribose sugar to which a phosphate group is attached. Triplets of nucleotides (referred to as codons) code for each amino acid in a polypeptide, or for a stop signal. The term "codon" is also used for the corresponding (and complementary) sequences of three nucleotides in the mRNA into which the DNA sequence is transcribed.

Enriched: The term "enriched" means that the concentration of a material is at least about 2, 5, 10, 100, or 1000 times its natural concentration (for example), advantageously at least 0.01% by weight. Enriched preparations of about 0.5%, 1%, 5%, 10%, and 20% by weight are also contemplated.

EST (Expressed Sequence Tag): A partial DNA or cDNA sequence, typically of between 200 and 2000 sequential nucleotides, obtained from a genomic or cDNA library, prepared from a selected cell, cell type, tissue or tissue type, organ or organism, which corresponds to an mRNA of a gene found in that library. An EST is generally a DNA molecule sequenced from and shorter than the cDNA from which it is obtained.

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Examples of fluorophores that may be used are provided in U.S. Pat. No. 5,866,366 to Nazarenko et al., and include for instance: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Genomic DNA: The DNA found within the nucleus and containing an organism's genome, which is passed on to its offspring as information for continued replication and/or propagation and/or survival of the organism. The term can be used to distinguish between other types of DNA, such as DNA found within plasmids or organelles.

High throughput genomics: Application of genomic or genetic data or analysis techniques that use microarrays or other genomic technologies to rapidly identify large numbers of genes or proteins, or distinguish their structure, expression or function from normal or abnormal cells or tissues. It is particularly contemplated that high throughput genomics in some instances will include the detection or differentiation of polymorphisms between two individuals or reference samples, or between an individual and a reference sample.

Human Cells: Cells obtained from a member of the species *Homo sapiens*. The cells can be obtained from any source, for example peripheral blood, urine, saliva, tissue biopsy, surgical specimen, amniocentesis samples and autopsy material. From these cells, genomic DNA, cDNA, mRNA, RNA, cRNA, and/or protein can be isolated or generated.

Hybridization: Nucleic acid molecules that are complementary to each other hybridize by hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other.

"Specifically hybridizable" and "complementary" are terms that indicate a sufficient degree of complementarity such that stable and specific binding occurs between the oligonucleotide and the DNA or RNA or PNA target. An oligonucleotide need not be 100% complementary to its target nucleic acid sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, for example under physiological conditions in the case of in vivo assays, or under conditions in which the assays are performed.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. in *Molecular Cloning: A Laboratory Manual*, Cold Spring Harbor Laboratory Press (1989), chapters 9 and 11, herein incorporated by reference.

In vitro amplification: Techniques that increase the number of copies of a nucleic acid molecule in a sample or specimen. An example of in vitro amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: Detectable marker or reporter molecules, many of which can be attached to nucleic acids. Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as discussed below, but generally refers to the subset of constitutional alterations that have arisen within the past few generations in a kindred and that are not widely disseminated in a population group. In particular embodiments, the term is directed to those constitutional alterations that have major impact on the health of individuals having the mutation.

Nucleic acid: A deoxyribonucleotide or ribonucleotide polymer in either single or double stranded form, and unless otherwise limited, encompassing known analogues of natural nucleotides that hybridize to nucleic acids in a manner similar to naturally occurring nucleotides.

Nucleic acid array: An arrangement of nucleic acids (such as DNA or RNA) in assigned locations on a matrix, such as that found in cDNA arrays, or in the herein described genomic tag arrays.

Nucleic acid molecules representing genes: Any nucleic acid, for example DNA (intron or exon or both), cDNA or RNA, of any length suitable for use as a probe or other indicator molecule, and that is informative about the corresponding gene. In particular embodiments, there are provided genomic tags, generated through restriction enzyme digestion of genomic DNA, which are useful as nucleic acid molecules that represent genes, parts of genes, or polymorphisms or variants in genes or other genomic sequences.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear single-stranded polynucleotide sequence ranging in length from 2 to about 5,000 bases, for example a polynucleotide (such as DNA or RNA) which is at least 6 nucleotides, for example at least 10, 12, 15, 18, 20, 25, 50, 100, 200, 1,000, or even 5,000 nucleotides long. Oligonucleotides are often synthetic but can also be produced from naturally occurring polynucleotides.

An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules. Such analog molecules may also bind to or interact with polypeptides or proteins.

Peptide Nucleic Acid (PNA): An oligonucleotide analog with a backbone comprised of monomers coupled by amide (peptide) bonds, such as amino acid monomers joined by peptide bonds.

Plant cells: Cells obtained from any member of the Plantae Kingdom, a category which includes, for example, trees, flowering and non flowering plants, grasses, and *Arabidopsis*. The cells can be obtained from any part of the plant, for example roots, leaves, stems, or any flower part. From these cells, nucleic acid (including DNA, RNA, and so forth) and/or protein can be isolated.

Polymorphism: Variant in a sequence of a gene, or any genomic sequence, usually carried from one generation to another in a population. Polymorphisms can be those variations (nucleotide sequence differences) that, while having a different nucleotide sequence, produce functionally equivalent gene products, such as those variations generally found between individuals, different ethnic groups, and geographic locations. The term polymorphism also encompasses variations that produce gene products with altered function, i.e., variants in the gene sequence that lead to gene products that are not functionally equivalent. This term also encompasses variations that produce no gene product, an inactive gene product, a truncated gene product, or increased or increased activity gene product.

It is contemplated herein that polymorphisms may be both single nucleotide changes (e.g., single nucleotide polymorphisms, SNPs) or short deletions or insertions within a genomic sequence.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNAses, a change in the availability of a site for cleavage by a restriction endonuclease, either the formation of a new site, or lose of a site, and so forth).

Processing (of a sample of nucleic acid): Any laboratory procedure that is carried out to alter or affect a nucleic acid molecule or sample of nucleic acids. This includes, for instance, digestion of the nucleic acid with a specific or non-specific nuclease, ligation of a one or more nucleotide bases, oligonucleotide(s), or polynucleotide (such as a vector) (or both) to the nucleic acid, sequencing of a nucleic acid, modification of one or more bases within a nucleic acid (e.g., chemical modification), purification of a nucleic acid or collection thereof from the milieu in which it is (they are) found, otherwise altering that milieu (for instance, by changing the pH, temperature, time of incubation, salt concentration, and so forth), or in any way affecting the nucleic acid sample.

A nucleic acid sample (such as a DNA sample) that has been processed (in one or more ways, or using one or more specific procedures) can be referred to as a processed sample of nucleic acids. More specifically, by way of example a nucleic acid sample or mixture of nucleic acids that has been treated with a nuclease can be referred to as a nucleased sample (e.g., a DNA sample may be referred to as a DNAsed sample after it is treated with DNAse). A nucleic acid that has been "polished" so that there are no overhanging nucleotides (either by remove of the overhang, or filling in with a ligase or polymerase) can be referred to either as polished or blunted, or "blunt-ended" (in reference to the blunt (non-overhanging) ends after the process.

Purified: The term purified does not require absolute purity; rather, it is intended as a relative term. Thus, for example, a purified nucleic acid preparation is one in which the specified protein is more enriched than the nucleic acid is in its generative environment, for instance within a cell or in a biochemical reaction chamber. A preparation of substantially pure nucleic acid may be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid content of the preparation.

The term purified, in some embodiments, refers to the separation of nucleic acids of certain sizes or size ranges from a mixture of, for instance, fragmented longer nucleic acids. Thus, for instance, it is appropriate to refer to purifying from a preparation of genomic DNA a collection of nucleic acid fragments of a set range of length, such as about 200 bp to about 500 bp, about 500 bp to about 1000 bp, about 750 bp to about 1500 bp, about 1000 bp to about 2000 bp, about 1000 bp, about 1500 bp, about 2000 bp, about 3000 bp, and so forth. Preparation of relatively long sets of fragments (e.g., 1 kb or more, 2 kb or more, 3 kb or more, 5 kb or more, and so forth) are also contemplated. In each instance, the reference to a purified preparation (e.g., a purified preparation of genomic fragments of about 1 kb) does not require absolute purity with regard to the length of the molecules. Rather, as discussed above, this refers to a preparation wherein the specified nucleic acid length represents the length of at least 50% of the molecules in a mixed preparation. In certain embodiments, a substantially pure nucleic acid of a specified length will contain at least 60%, at least 70%, at least 80%, at least 85%, at least 90%, or at least 95% or more nucleic acid molecules of approximately the specified length within the total nucleic acid content of the preparation.

Recombinant: A recombinant nucleic acid is one that has a sequence that is not naturally occurring or has a sequence that is made by an artificial combination of two otherwise separated segments of sequence, or a sequence that has been generated through a naturally occurring or induced genetic recombination event. Artificial recombinant combinations can be accomplished by chemical synthesis or, more commonly, by the artificial manipulation of isolated segments of nucleic acids, e.g., by genetic engineering techniques.

Recombinant line: A line or strain, or individual, set of individuals, etc., that differs from a parent thereof by recombination within its genome. Recombination is generally the process by which offspring derive a combination of genes different from that of either parent. By way of example, this can occur by crossing over. Representative examples provided herein are recombinant lines of *Drosophila*. In humans, children are 'recombinant lines' of the parents, in that the paternal and maternal chromosomes are each combinations of the different grandparent chromosomes. Similarly, a field test of a crop will typically be a test of many different recombinants (each of which could be used to give rise to a recombinant line) derived from a set of parents. So in any situation where there is a set of progeny, and some have a trait and some do not, those two groups could be compared on an array such as those described herein, for parental chromosome material in common within a group and different between groups.

Regulatory sequences or elements: These terms refer generally to a class of DNA sequences that influence or control expression of genes. Included in the term are promoters, enhancers, locus control regions, boundary elements/insulators, silencers, Matrix attachment regions (also referred to as scaffold attachment regions), repressor, transcriptional terminators, origins of replication, centromeres, and meiotic recombination hotspots. Promoters are sequences of DNA near the 5' end of a gene that act as a binding site for RNA polymerase, and from which transcription is initiated. Enhancers are control elements that elevate the level of transcription from a promoter, usually independently of the enhancer's orientation or distance from the promoter. Locus control regions (LCRs) confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also know as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. Matrix attachment regions (MARs), also known as scaffold attachment regions, are sequences within DNA that bind to the nuclear scaffold. They can affect transcription, possibly by separating chromosomes into regulatory domains. It is believed that MARs mediate higher-order, looped structures within chromosomes. Transcriptional terminators are regions within the gene vicinity that RNA polymerase is released from the template. Origins of replication are regions of the genome that, during DNA synthesis or replication phases of cell division, begin the replication process of DNA. Meiotic recombination hotspots are regions of the genome that recombine more frequently than the average during meiosis.

RNA: A typically linear polymer of ribonucleic acid monomers, linked by phosphodiester bonds. Naturally occurring RNA molecules fall into three classes, messenger (mRNA, which encodes proteins), ribosomal (rRNA, components of ribosomes), and transfer (tRNA, molecules responsible for transferring amino acid monomers to the ribosome during protein synthesis). Total RNA refers to a heterogeneous mixture containing all three types of RNA molecules.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of nucleic acid or amino acid sequences will possess a relatively high degree of sequence identity when aligned using standard methods. This homology will be more significant when the orthologous proteins or nucleic acids are derived from species which are more closely related (e.g., human and chimpanzee sequences), compared to species more distantly related (e.g., human and C. elegans sequences). Typically, orthologs are at least 50% identical at the nucleotide level and at least 50% identical at the amino acid level when comparing human orthologous sequences.

Methods of alignment of sequences for comparison are well known. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, Gene, 73:237-44, 1988; Higgins & Sharp, CABIOS 5:151-3, 1989; Corpet et al., *Nuc. Acids Res.* 16:10881-90, 1988; Huang et al. *Computer Appls. Biosci.* 8, 155-65, 1992; and Pearson et al., *Methyl. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx. Each of these sources also provides a description of how to determine sequence identity using this program.

Homologous sequences are typically characterized by possession of at least 60%, 70%, 75%, 80%, 90%, 95% or at least 98% sequence identity counted over the full length alignment with a sequence using the NCBI Blast 2.0, gapped blastp set to default parameters. Queries searched with the blastn program are filtered with DUST (Hancock and Armstrong, *Comput. Appl. Biosci.* 10:67-70, 1994). It will be appreciated that these sequence identity ranges are provided for guidance only; it is entirely possible that strongly significant homologs could be obtained that fall outside of the ranges provided.

Nucleic acid sequences that do not show a high degree of identity may nevertheless encode similar amino acid sequences, for instance due to the degeneracy of the genetic code. It is understood that changes in nucleic acid sequence can be made using this degeneracy to produce multiple nucleic acid sequences that all encode substantially the same protein.

An alternative indication that two nucleic acid molecules are closely related is that the two molecules hybridize to each other under stringent conditions, as described under "specific hybridization."

Single Nucleotide Polymorphism (SNP): A single base (nucleotide) difference in a DNA sequence among individuals in a population. SNPs can be causative (actually involved in or influencing the condition or trait to which the SNP is linked) or associative (linked to but not having any direct involvement in or influence on the condition or trait to which the SNP is linked).

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Traditional hybridization with a target nucleic acid molecule labeled with [$^{32}$P]-dCTP is generally carried out in a solution of high ionic strength such as 6×SSC at a temperature that is 20-25° C. below the melting temperature, $T_m$, described below. For Southern hybridization experiments where the target DNA molecule on the Southern blot contains 10 ng of DNA or more, hybridization is typically carried out for 6-8 hours using 1-2 ng/ml radiolabeled probe (of specific activity equal to $10^9$ CPM/μg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at $T_m$ 50% of the probes are occupied at equilibrium. The $T_m$ of such a hybrid molecule may be estimated from the following equation (Bolton and McCarthy, *Proc. Natl. Acad. Sci. USA* 48:1390, 1962):

$$T_m = 81.5°C. - 16.6(\log_{10}[Na^+]) + 0.41(\% \text{ G+C}) - 0.63(\% \text{ formamide}) - (600/1)$$

where 1=the length of the hybrid in base pairs.

This equation is valid for concentrations of $Na^+$ in the range of 0.01 M to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from a cDNA (with a hypothetical % GC of 45%), a calculation of hybridization conditions required to give particular stringencies may be made as follows: For this example, it is assumed that the filter will be washed in 0.3× SSC solution following hybridization, thereby: $[Na^{+}]=0.045$ M; % GC=45%; Formamide concentration=0; 1=150 base pairs; $T_m = 81.5 - 16.6(\log_{10}[Na^+]) + (0.41 \times 45) - (600/150)$; and so $T_m = 74.4°C$.

The $T_m$ of double-stranded DNA decreases by 1-1.5° C. with every 1% decrease in homology (Bonner et al., *J. Mol. Biol.* 81:123, 1973). Therefore, for this given example, washing the filter in 0.3×SSC at 59.4-64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target cDNA molecule will not hybridize. The above example is given entirely by way of theoretical illustration. It will be appreciated that other hybridization techniques may be utilized and that variations in experimental conditions will necessitate alternative calculations for stringency.

Stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

The following is an exemplary set of hybridization conditions and is not meant to be limiting:

| Very High Stringency (detects sequences that share 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (detects sequences that share 80% identity or greater) | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (detects sequences that share greater than 50% identity) | |
|---|---|
| Hybridization: | 6x SSC at RT to 55° C. for 16-20 hours |
| Wash at least twice: | 2x-3x SSC at RT to 55° C. for 20-30 minutes each. |

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Transcription levels can be quantitated absolutely or relatively. Absolute quantitation can be accomplished by inclusion of known concentrations of one or more target nucleic acids (for example control nucleic acids or with a known amount the target nucleic acids themselves) and referencing the hybridization intensity of unknowns with the known target nucleic acids (for example by generation of a standard curve).

Subject: Living, multicellular, vertebrate organisms, a category that includes both human and veterinary subjects for example, mammals, birds and primates.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety, whether or not such incorporation is made at the point of citation. In case of conflict, the present specification, including explanations of terms, will control. In addition, the materials, methods, and examples are illustrative only and not intended to be limiting.

III. Overview of Several Embodiments

There is provided in a first embodiment a method of nucleotide polymorphism (or variant) discovery, which method involves isolating fragment tags near restriction sites from genomic (or other) DNA; hybridizing the tags from two individuals or samples to a nucleic acid array (or other detection platform, such as a collection of beads loaded with target nucleic acid molecules); and detecting differential hybridization, where differential hybridization indicates a sequence difference (nucleotide polymorphism) between the two individuals or samples.

There is provided in a second embodiment a method of nucleotide polymorphism (or variant) discovery, which method involves annealing to each other restriction enzyme-digested genomic DNA fragments from two individuals or samples; adding components for primer extension, in presence of a label; allowing extension along one or more differentially cut genomic DNA fragments, which extension incorporates the label into the extension products; and detecting labeled extension products, if such are generated, where a labeled extension product is indicative of a sequence difference (nucleotide polymorphism) between the two individuals or samples.

Yet other embodiments are collections of nucleic acids, particularly arrays, such as nucleic acid arrays and microarrays, and bead libraries. One example of such is a restriction site tag array (or library), which comprises as features two or more genomic restriction fragment tags from at least one individual. Another collection of nucleic acid molecules provided herein is a subtractive restriction site tag array (or library), which includes as features two or more genomic restriction fragment tags selected at least in part through subtractive hybridization of DNA from two individuals or samples in order to enrich the feature set on the collection/array/library for genomic restriction fragment tags that differ between the two individuals or samples.

Methods of use of nucleic acid collections, such as arrays and bead libraries, as described herein are also provided. For instance, contemplated and described herein is use of restriction site tag arrays or subtractive restriction site tag arrays, for instance to detect a nucleotide polymorphism between the genomes of two individuals or two samples. Also described are hybridization methods for polymorphism (or variant) identification, mapping and/or analysis, which methods comprise hybridizing a first and a second single-stranded nucleotide molecule (e.g., labeled nucleotide molecules) to a restriction site tag array or a subtractive restriction site tag array. By way of example, hybridization assays will in some instances include contacting at least one labeled target nucleic acid sample with an array, such as a restriction site tag array or a subtractive restriction site tag array (or library), under conditions sufficient to produce a hybridization pattern; and detecting the hybridization pattern.

In yet another embodiment the is provided a method that includes isolating fragment tags (for instance, tags of about 1 kb, though other lengths are contemplated) near restriction sites from genomic or other DNA; hybridizing the tags from two individuals or samples to a collection of nucleic acid elements (for instance, a nucleic acid array or a bead library); and detecting differential hybridization, where differential hybridization indicates a sequence difference (nucleotide polymorphism) between the two individuals or samples. By way of example, isolating fragment tags in some cases involves contacting a preparation of genomic or other DNA with a restriction endonuclease; subjecting the preparation of genomic DNA shearing force to fragment the DNA; and isolating DNA fragments from the resulting preparation based at least in part on their length, which are the fragment tags, wherein shearing and digesting the genomic (or other) DNA with the restriction endonuclease can occur in either order or concurrently. The collection of nucleic acid elements in various examples comprises genomic DNA fragments, cDNAs or fragments thereof, synthetic nucleic acid sequences, or a combination thereof.

Also provided is a method that involves shearing genomic (or other) DNA to fragments about 3-5 kb in length (though other length ranges could be selected); filling in any resultant overhanging ends on the fragments; digesting the sheared (and back filled) DNA with a restriction enzyme, to produce a collection of DNA fragments at least some of which have a restriction site at one end and a blunt end on the other; isolating from the collection DNA fragments about 1 kb in length (though longer and shorter fragment sets are contemplated); ligating a linker to the sheared DNA at the restriction site to produce linkered DNA fragments; isolating Tinkered fragments; and recovering the DNA fragments by digesting away the linker. These fragments are indicative of the sequence of the starting nucleic acids, for instance with regard to polymorphisms or other variants, due to differential enzyme digestion.

Also provided are restriction site tag arrays and bead libraries, comprising as features of the array or as nucleic acid components of members of the bead library two or more (or a much larger number) genomic restriction fragment tags from at least one individual.

Methods of generating restriction site tag arrays or bead libraries (or other collects of restriction site tags) are described. In examples of such methods, a collection of genomic DNA fragments is produced from an individual, at least some fragments of which have a restriction site at one end and blunt at the other end, in either order or concurrently: shearing a preparation of genomic DNA from the individual to fragments about 3-5 kb in length; and digesting the preparation of genomic DNA with a restriction enzyme. From the collection of genomic DNA fragments, a subset of DNA fragments about 1 kb in length are isolated, thereby producing a tag set; optionally fragments of the tag set are amplified. The fragments of the tag set (which have optionally been amplified) are then used as features on the array or in the bead library, or more generally as members in the collection of nucleic acid molecules.

Subtractive restriction site tag arrays and bead library are also provided, comprising as features of the array or as nucleic acid components of members of the bead library two or more genomic restriction fragment tags selected at least in part through subtractive hybridization of DNA from two individuals or samples in order to enrich the feature set on the array or in the bead library for genomic restriction fragment tags that differ between the two individuals or samples. By way of example, such subtractive arrays/libraries are produced using a method that involves first producing a collection of genomic DNA fragments from each of the two individuals or samples, at least some fragments of which have a restriction site at one end and blunt at the other by, in either order or concurrently: shearing a preparation of genomic DNA from each individual to fragments about 3-5 kb in length; and digesting each preparation of genomic DNA with a restriction enzyme. DNA fragments about 1 kb in length are isolated, thereby producing a tag set from each individual or sample, and subtractive hybridization is performed between the two tag sets, to produce a collection of genomic restriction fragment tags that differ between the two individuals or samples (differential fragment tags). The collection of genomic restriction fragment tags (which optionally can be amplified) are then used as features on the array or in the bead library.

Methods of using arrays, bead libraries, and other nucleic acid (e.g., fragment tag or tag set) collections are also provided, including methods for detecting a nucleotide difference (or similarity) between the genomes of two individuals or two samples.

Hybridization methods for polymorphism identification or analysis are also provided, which involve hybridizing a first and a second single-stranded nucleotide molecule, or a first and second mixture of single-stranded nucleotide molecules, to an array or bead library (or other collection of nucleic acids) described herein, and detecting the presence of differential hybridization. In an example hybridization assay, steps include contacting at least one labeled target nucleic acid sample with an array or bead library (or other collection) under conditions sufficient to produce a hybridization pattern; and detecting the hybridization pattern.

There is also provided a method, comprising annealing to each other restriction enzyme-digested genomic DNA fragments from two individuals or samples; adding components for primer extension, in presence of a label capable of being integrated into resultant extension products; allowing extension along one or more differentially cut genomic DNA fragments, which extension incorporates the label into the extension products; and detecting labeled extension products, if such are generated, where a labeled extension product is indicative of a sequence difference (for instance, a nucleotide polymorphism) between the two individuals or samples.

Yet additional embodiments are methods that involve identifying one or more genomic tags as polymorphic between two individuals or populations using any one of the methods described herein; identifying a tag of interest by selecting a polymorphic spot mapping within the chromosomal region of interest and showing the presence of a tag in the population not having the trait of interest. designing amplification primers, one of which is specific for the sequence of the tag of interest, the other corresponding to sequence in a DNA adapter sequence (e.g., a relatively short nucleic acid, such as a linker, part of which complements the overhanging nucleotide sequence of the restriction site used in generating the tag and which includes a sequence to which an amplification primer can bind) ligated to the restriction site, isolating tags from a bulk population that exhibits the trait of interest; and amplifying the isolated tags using the amplification primers.

IV. Methods for Detection of Polymorphisms

Described herein are methods for SNP (or other sequence variation) discovery and mapping and genotyping. These methods are substantially based on commonly used molecular biology protocols, do not require prior knowledge of the nucleic acid population (e.g., genome) sequence to be analyzed, can be used to detect SNPs in any number of different individuals, and scale well so that increased time and effort yield more SNPs and more genotypes. The provided methods make mapping mutations from genetic screens more routine, and are expected to spur the development of technologies for association studies of disease mapping and other more complex applications in humans. In overview, the provided polymorphism detection methods exploit differential restriction endonuclease digestion, which is detected using various means, in order to identify the presence of polymorphisms. Detection methods include, for instance, detection of differential hybridization due to differential digestion patterns, with or without primer extension to differentially label subpopulations of fragments.

A first method involves use of a restriction enzyme to cleave a target DNA sequence, for instance into size limited (e.g., ~1 kb, though other lengths are contemplated) fragments; these fragments are referred to herein as tags, genomic tags, or genomic restriction tags. Optionally, a subset of all of the fragments generated by digesting a sheared or otherwise fragmented genomic preparation can be selected (e.g., purified) for use in these methods. In individuals where a nucleotide polymorphism disrupts a recognition sequence of the restriction endonuclease, the associated tag will be absent. Alternatively, looked at in a different way, a polymorphism may generate a new recognition sequence for the restriction endonuclease, thereby generating a new fragment or removing a fragment because the original fragment is now too short to be selected. Comparison of digested DNA from two samples (e.g., two individuals) can be used to detect polymorphisms. For instance, labeled tags from two samples are hybridized to an array, and the presence of polymorphisms is detected as strong differential hybridization of the labeled DNA fragments on array elements.

A second method identifies polymorphisms by annealing restriction enzyme-digested genomic DNA from two individuals to each other. If nucleotide polymorphisms disrupt the restriction site in one of the two individuals, then the site of polymorphism will generate two short fragments (from one individual) bound to a longer (undercut) single fragment (from the other individual). A similar situation pertains if a polymorphism generates a new restriction enzyme recognition site, as will be apparent. One of the short fragments annealed to the longer fragment from the other individual is able to act as a primer for extension by DNA polymerase, allowing the incorporation of a label (e.g., fluorescent dye-linked nucleotides) near the polymorphism site. Hybridization of labeled DNA to microarrays allows polymorphism detection and discovery at the array elements with strong hybridization signal intensity, as these elements will have bound the newly synthesized sequences that correspond to the sequence containing the polymorphism.

Though not essential for analysis of the tag fragments generated by the provided methods, there are also provided tag-specific arrays (referred to, for instance, as genomic tag arrays), and tag-specific bead libraries, that can be beneficial in the analysis and detection of polymorphism. A genomic tag array or bead library consists of a collection of genomic DNA sequences flanking sites of digestion for a particular restriction enzyme in the genome. It is recognized that in most situations, such an array or library will contain an undersampling of all possible tags. For example, there may be 500,000 to 1 million EcoRI sites in the human genome; digestion would generate twice that number of tags (one arising from either side of the cut). Often, only a maximum of about $\frac{1}{10}^{th}$ of these would be placed on an array (though higher numbers are contemplated); thus, only a small percentage of tags would have its partner flanking tag (from directly opposite the restriction digestion) also on the same array.

For subtractive arrays and bead libraries as discussed below, very large arrays or collections of beads would contain a higher percentage of paired flanking tags. While the presence of such redundancy would lead to more confidence in interpreting a signal at a particular SNP locus, only one of the tags needs to be present to assay any single location. When the experimental and array (or bead library) restriction sites match, each element is capable of detecting a restriction site tag, or an extension from restriction site polymorphism. Such an array (or bead library) contains a number of elements that are in common between the genomes of interest and other elements unique to a genome.

Yet another type of array provided herein is a very efficient array that contains only (or substantially only) elements that differ between individuals. This is generated using the tags that remain after the tags from the two individuals undergo a round of subtractive hybridization, a procedure that removes DNA in common. In such a subtractive genomic tag array, a 5000 element array could assay 5000 polymorphism differences between individuals.

The various approaches described herein allow SNPs between any two individuals (or any two samples, such as an individual and a reference sample) to be rapidly detected at higher numbers than would be possible from all but the most specialized efforts available prior to this teaching. The described approaches are flexible enough to be used in an organism for which the genome sequence is not yet available, allowing SNP mapping of traits in a variety of organisms. Furthermore, they allow the establishment of SNP maps for laboratory lines or natural populations in which SNP alleles exist at different frequencies compared to SNP maps already created. Thus, these techniques could impact a variety of efforts to map mutations or natural alleles that affect phenotypes or lead to disease.

Related techniques are described in U.S. patent application Ser. No. 10/236,598, published as US2004/0048257, which is incorporated herein by reference in its entirety.

It will readily be appreciated that the methods (and arrays and other nucleic acid collections) described herein can be used with nucleic acids from any source or subject, including animals, plants, microbes, and fungi. Nucleic acid molecules that can be analyzed using disclosed methods include any nucleic acid molecule capable of (or believed to) including at least one variant (e.g., polymorphism or mutation) when compared to a reference or other sample. Though the provided methods are in some instances adapted for and explained in the context of genomic DNA (including chromosomal DNA), other nucleic acid molecules that can be analyzed include, without limitation, plasmid DNA, human artificial chromosomes (HACs), yeast artificial chromosomes (YACs), bacterial artificial chromosomes (BACs), P1-derived artificial chromosomes (PACs), cosmids and fosmids. In particular contemplated examples, analyzed nucleic acid molecules are genomic DNA. Genomic DNA may be obtained, for example, from one or more cells by methods known to those of ordinary skill in the art (for example, kits for this purpose are commercially available from Promega, Roche Biochemical, Bio-Nobile, Brinkmann Instruments, BIO-LINE, MD Biosciences, and numerous other commercial suppliers; see, also, Sambrook et al., *Molecular Cloning: A Laboratory Manual*, New York: Cold Spring Harbor Laboratory Press, 1989; Ausubel et al., *Current Protocols in Molecular Biology*, New York: John Wiley & Sons, 1998).

Genomic DNA can also be obtained from any biological sample that may be obtained directly or indirectly from a subject (e.g., a medical or veterinarian subject), including whole blood, plasma, serum, tears, bone marrow, lung lavage, mucus, saliva, urine, pleural fluid, spinal fluid, gastric fluid, sweat, semen, vaginal secretion, sputum, fluid from ulcers and/or other surface eruptions, blisters, abscesses, and/or extracts of tissues, cells or organs. The biological sample may also be a laboratory research sample such as a cell culture supernatant. Sample are collected or obtained using methods well known to those ordinarily skilled in the art.

In specific examples, genomic DNA is eukaryotic genomic DNA. Genomic DNA can be obtained from an organism (or cells thereof) for which the sequence of genomic DNA is substantially known, including for instance, human (*Homo sapiens*), mouse (*Mus musculus*), rat (*Rattus norvegicus*), zebrafish (*Danio rerio*), *Caenorhabditis elegans*, *Drosophila melanogaster*, *Anopheles gambiae*, *Arabidopsis thaliana*, lotus (e.g., *Lotus corniculatus* var. *japonicus*), tomato (e.g., *Lycopersicon esculentum*), soybean (*Glycine max*), corn (*Zea mays*), rice (e.g., *Oryza sativa*), or cottonwood (e.g., *Populus* spp.) genomic DNA. In addition, however, it is a particular benefit of the provided methods that the genome sequence need not be know for the methods to provide polymorphism or variant information, including distinguishing individuals or populations, examples of which are provided.

The methods (arrays, etc.) provided herein can be used in the analysis of plant nucleic acids. Additional representative, non-limiting example plants include *Arabidopsis*; field crops (e.g. alfalfa, barley, bean, clover, corn, cotton, flax, lentils, maize, pea, rape/canola, rice, rye, safflower, sorghum, soybean, sunflower, tobacco, and wheat); vegetable crops (e.g. asparagus, beet, *brassica* generally, broccoli, Brussels sprouts, cabbage, carrot, cauliflower, celery, cucumber (cucurbits), eggplant, lettuce, mustard, onion, pepper, potato, pumpkin, radish, spinach, squash, taro, tomato, and zucchini); fruit and nut crops (e.g. almond, apple, apricot, banana, blackberry, blueberry, cacao, cassaya, cherry, citrus, coconut, cranberry, date, hazelnut, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); tree woods and ornamentals (e.g. alder, ash, aspen, azalea, birch, boxwood, camellia, carnation, chrysanthemum, elm, fir, ivy, jasmine, juniper, oak, orchid, palm, poplar, pine, redwood, rhododendron, rose and rubber). By way of example, the polymorphism detection methods described herein can be used to detect differences between (or similarities between) plants, including identifying related (or unrelated) plant specimens.

Specific embodiments will be discussed more fully below, and in the Examples that follow.

V. Restriction Site Tags for Polymorphism Discovery and Mutation Mapping

Using restriction site tags for polymorphism discovery and mutation mapping is conceptually simple, and requires little prior knowledge of the organism's genome. The detection of SNPs and other polymorphisms depends on the fact that a nucleotide polymorphism may (and statistically will) disrupt the recognition sequence of a restriction endonuclease (or generate a new recognition site). Cutting genomic DNA with a restriction enzyme that recognizes, for instance, a 6-base-pair sequence (a 6-cutter enzyme) will produce many thousands of genomic fragments, essentially all of which are flanked by the restriction site. A small region of DNA flanking the restriction site is then isolated, so that the presence or absence of the site can be detected. By way of example, this system can be referred to as Genome-wide RFLP Identification and Segregation (GRIdS). Alternatively, the resultant DNA tags can be referred to as RAD (Restriction site Associated DNA) markers, and the corresponding collections of tags as RAD arrays or libraries.

One specific protocol employed to generate restriction site tags is as follows (also see FIG. 1):

1) Shear genomic DNA to fragments 3-5 kb in length and fill in ends.
2) Digest the sheared DNA with a restriction enzyme, producing a collection of fragments at least some of which have a restriction site at one end and a blunt end on the other.
3) Isolate DNA fragments 1 kb in length by, for instance, gel purification.
4) Ligate a biotinylated linker to the sheared DNA at the restriction site.
5) Isolate the biotinylated linker and attached DNA, thereby isolating only those fragments that had at least one end with a restriction site.
6) Recover the purified DNA fragments by digesting away the linker.

The order of at least certain of these steps is not essential. For instance, shearing of the genomic DNA, though noted above to be a first step, has successfully been carried out later in the procedure. By way of specific example, shearing can be carried out after digestion with the restriction enzyme. See, for instance, Example 1 below. It is believed that the order of digestion by an RE and shearing is immaterial.

The final mixture now contains short tags from near the existing restriction endonuclease cut sites. If the process is repeated on a second individual, a similar collection of tags is generated. However, on one hand, any restriction site containing a polymorphism that destroys recognition by the selected RE in the second individual will not create a fragment of DNA that can be ligated to a biotinylated linker, and thus no tags for that locus will be present in the purified DNA. If a polymorphism created a restriction site in the second individual where one did not exist in the first individual, then a tag associated with the genomic DNA near that locus will be present in the second individual's tag mixture but not the first individual's mixture.

The presence of these RE tags can be detected in various ways, examples of which are described herein. In a first embodiment, the differential RE tags are detected, and optionally quantified, on a microarray by differential labeling (e.g., fluorescent labeling). For example, the genomic tags from individual 1 could be labeled with Cy-3 and the tags from individual 2 labeled with Cy-5. A spot on the array showing a strong signal in one channel but not the other would indicate that a polymorphism exists at that locus. Most array spots would have roughly equal intensity, as most restriction sites would not be polymorphic. The creation of short tags around the restriction site is important to make the absence of a restriction site detectable. If the two genomes were merely digested and labeled, then all genomic DNA would be available for hybridization to the microarray, resulting in equal intensity signals at all array elements.

The frequency by which there will be a difference in tag representation depends on the length of the restriction site sequence and the frequency of nucleotide polymorphisms between the two individuals. An individual polymorphic at a rate of 1 nucleotide in 100 will have an altered 6-basepair restriction site once out of every 16 occurrences of the site. This suggests a detectable tag difference could occur every 64 kb, if the restriction site occurs every 4 kb on average. A polymorphism rate of 1 in 500 would decrease the resolution to 320 kb. For simplicity, we will assume a polymorphism rate (single nucleotide polymorphisms and small insertion or deletions) of 1 every 100 nucleotides. For that rate, a genomic DNA microarray capable of detecting all tag differences in the *Drosophila melanogaster* genome would identify ~1800 SNPs in a single experiment.

There are many alternatives available for detecting tag differences, as will be recognized by one of ordinary skill. In order of increasing ability to detect tag differences, selected possibilities include small-scale sequencing, expression microarrays, restriction tag microarrays or other assayable nucleic acid collections (discussed below, in Section VII), and tiling path genomic microarrays.

The most common commercially available resource for genomics is an expression microarray composed of random cDNAs that are PCR-amplified and spotted onto glass or another substrate. These are expected to allow detection of tag differences at a reasonable scale. The *Drosophila* community, for instance, has several options for expression arrays, including oligos in the 70-mer range, short PCR fragments from genomic primers, and cDNA collections.

With expression arrays, tag differences far from the genomic location of the spotted material will not be detected, decreasing the resolution of the SNP map. For example, the Incyte primer set produces ~15,000 amplicons of 400-700 basepairs in length. The amplicons vary greatly in density across the genome, but average one every 8,000 basepairs. Since only restriction sites near an amplicon will create a tag capable of hybridizing to the spotted material, only one out of every three amplicons would detect a possible tag, and only one of every 50 amplicons detect a tag difference, for a resolution of 400 kb between detectable tag differences. Spotted long oligos would decrease this resolution, as the spotted target area would be decreased (70 basepairs versus 400-700 basepairs). Arrays of full-length cDNAs would increase the resolution, except they rarely represent the entire set of transcribed genes. However, for non-sequenced genomes, this is likely to be the most common platform for detection.

Arrays of genomic DNA provide a powerful platform for tag detection. By way of example, a genomic tiling path microarray made up of the 3 kb subclones used in sequencing the *Drosophila melanogaster* genome (Adams et al., *Science* 287(5461): 2185-95, 2000) has been generated for use with methods described herein. This example array is composed of ~65,000 spots with greater than 70% coverage of the *Drosophila* genome. Most of the gaps in coverage are less than 1 kb and are not likely to cause missing data by the methods described herein. The use of sequencing subclones allowed amplification of the different genomic inserts with the same PCR primers, and thus inexpensively create a tool that had previously only been available for much smaller genomes, such as yeast (Lieb et al., *Nat Genet.* 28(4): 327-34, 2001; Lee et al., *Science* 298(5594): 799-804, 2002). The entire clone set has been robotically picked through to create an optimal overlapping path (each clone is half covered by the preceding clone and half covered by the next clone), with greater coverage and a reduced number of spots.

For tag difference detection, the genomic array provides a nearly complete representation of restriction sites, and thus a possible resolution of (4 kb*16 sites between disruptive SNPs), or 64 kb. This resolution may be difficult to achieve in practice, as a significant percentage of 3 kb clones may include multiple restriction sites. If only one of the sites contained a SNP, then the signal hybridized at the spot would only decrease by half or more, making the SNP calls less certain.

There is also described herein a simple method to create a powerful microarray platform for mapping polymorphisms/SNPs (discussed in Section VII, for instance). If the short tags from the above method were ligated into a plasmid, transformed into bacteria, then singly picked and amplified, each spot on the resulting array would contain a restriction site tag matching the labeled material. Thus, the resolution would scale well with the number of sites picked, until repeat sampling of previously picked sites begins to affect coverage.

One of the probable uses of routine polymorphism/SNP detection in model organisms is the mapping of mutations from genetic screens. The use of SNP panels has greatly increased the speed of mapping, although only a few fly lines have been examined for SNPs. The methods described herein can be used to create genomic tags in lines commonly used for mutagenesis screens, such as the *Drosophila* lines FRT 82 and rucuca. The FRT 82 line is typically mutagenized; mapping of the mutation is then partly accomplished by creating recombinants with the visible marker line rucuca. The recombination breakpoint can be roughly mapped by the presence or absence of the visible markers.

Genomic DNA from the two *Drosophila* lines has been digested with the restriction enzyme BamHI. Although the choice of restriction enzyme is somewhat arbitrary, enzymes recognizing C-rich sites may detect more SNPs as many SNPs are C to T transitions. The genomic tags from the two lines have been hybridized to a genomic microarray, to determine which array elements can detect SNPs differing between the two lines. By the microarray assay described in Example 1, yellow array elements indicate a restriction site shared by both genomes, while red or green elements indicate the presence of restriction sites unique to one of the genomes.

Figure 2:
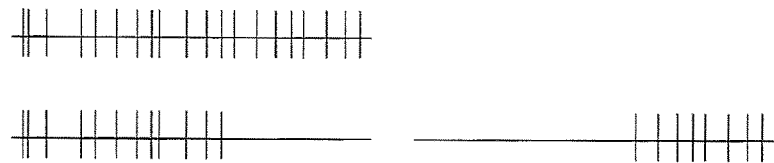
FIG. 2 illustrates identification of recombination breakpoints. Hybridization of tags from FRT 82 and rucuca identify potential SNPs along the chromosome (top, vertical lines). Hybridization of the recombinant versus FRT 82 will produce tag differences wherever the recombinant chromosome contains rucuca material (bottom left, vertical lines). Hybridization of the recombinant versus rucuca will produce tag differences wherever the recombinant chromosome contains FRT 82 material (bottom right, vertical lines).

Genomic tags from several different recombinant lines can be collected and hybridized to a microarray with, for instance, either the FRT 82 or the rucuca parental line in the other fluorescent channel. Areas where the chromosomes match genetic material are expected to create only yellow spots, whereas areas matching the other parental line are expected to have a pattern of tag differences identical to the initial array of the two parentals. Thus, the breakpoint of recombination should be where these two patterns switch modes, with hybridizations to each parent producing opposite patterns (see FIG. 2). From such microarray analyses, it is possible to make specific predictions about where the recombination breakpoints fall along the chromosome. To confirm these predictions, the genome near the predicted breakpoint can be examined, and areas on either side in the parental lines and recombinant lines sequenced to confirm the presence of SNPs disrupting restriction sites.

Figure 3:
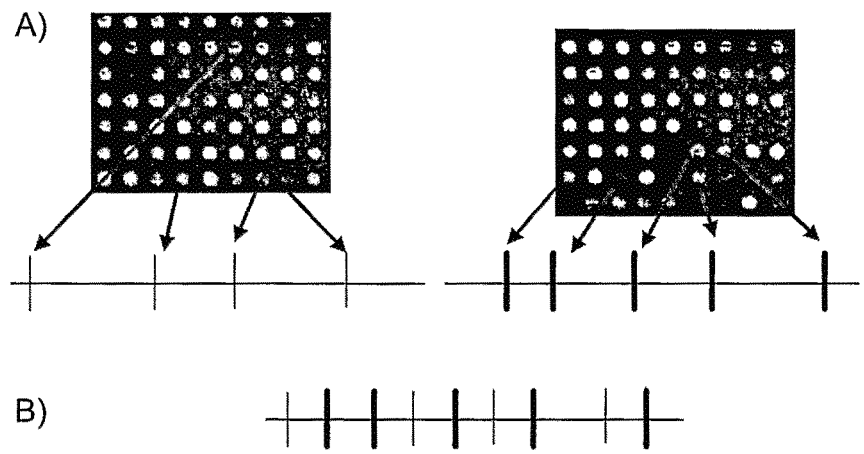
FIG. 3 illustrates that SNP detection is additive with different restriction enzymes.

The number of polymorphisms detected goes up with additional experiments using different restriction endonucleases. Different restriction enzymes would have a similar rate of SNP discovery, but different array elements would show differential hybridization with each different restriction endonuclease experiment. Thus, with repeated experiments, the total number of detectable SNPs could approach the number of elements on the array, with a correlated increase in mapping resolution (see FIG. 3).

By way of example, the creation of genomic tags using different 6-cutter restriction enzymes can be examined. Each enzyme would query a different set of possible SNPs in the genome, but yield essentially the same predicted recombination breakpoint. Thus, combining experiments using different restriction enzymes should create a SNP map with a greatly increased number of testable genotypes compared to using a single enzyme. It is proposed to use BamHI, NgoM IV, NotI and PvuI, though other 6-base cutters, or other combinations, will be apparent to those of ordinary skill in the art. Alternatively, 5-cutter restriction enzymes (many of which are known to those of ordinary skill in the art) can be examined to determine if, within a specific system, a shorter tag size is beneficial for discrimination of tag differences. Hybridization of the tags to different array platforms is expected to yield similar breakpoints, and each array platform can be evaluated for numbers of SNPs detected and signal consistency.

One potentially powerful aspect of the polymorphism mapping strategies described herein is the capability to perform a mapping hybridization of multiple recombinant lines on a single array. Hybridizing tag fragments from a single recombinant line versus tags from a parental line will allow the recombination breakpoints to be mapped at high resolution, but many recombinants would have to be hybridized to identify chromosomal regions in common and decrease the size of the region where the mutation is located.

Figure 4:
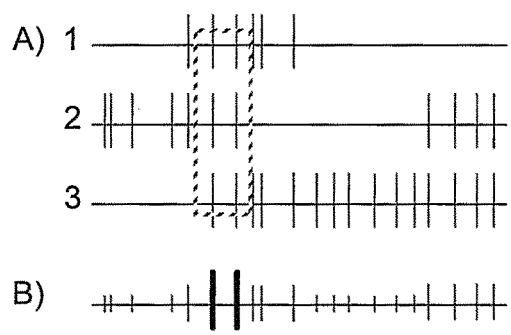
FIG. 4 illustrates mapping of bulk recombinants.
Figure 5:
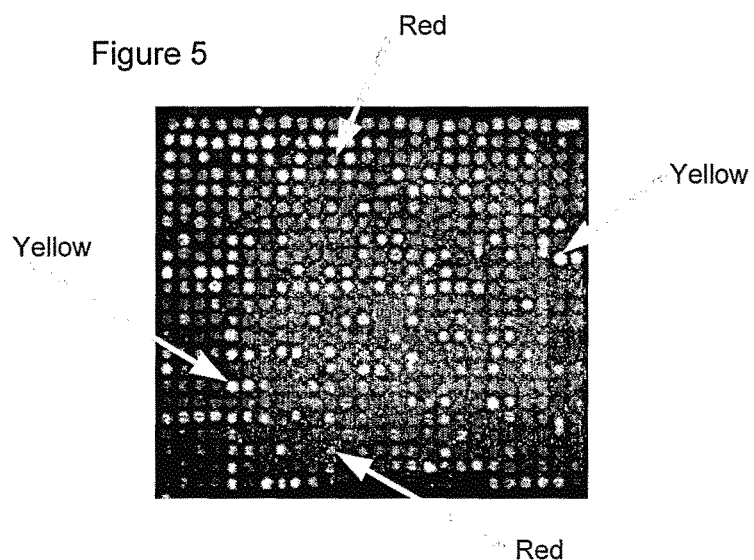
FIG. 5 is a microarray, illustrating a test of a representative restriction tag Protocol described in Example 1. Genomic DNA from FRT 82 and rucuca was digested with BamHI after shearing and hybridized to a genomic array (one block shown). Strong "red" and "green" spots were seen (representative ones of which are indicated with arrows), suggesting SNPs created differential tag presence.

If many recombinants are collected and have genomic tags isolated, either separately or in a single mixture, then the ratio of the signals in the two fluorescent channels at any array element would reflect the frequency in which that tag was present in the mixed population (see FIG. 4). So, for example, in an array of FRT 82, where a mutation was induced, versus mixed recombinants containing the mutation, the area surrounding the mutation will be present in all recombinants. As the distance from the mutation increases, the proportion of recombinant lines containing FRT 82 material at that tag will decrease. Therefore, spots approaching the FRT 82 versus rucuca ratio will be the area closest to the mutation, and array elements on either side of that area should show decreasing ratios, as more of the individuals contain rucuca material at that locus. Thus, identifying the likely region of a mutation entails examining array spot ratios and finding the peak of the curve. The resolution of the mapping is correlated with the number of recombinant lines tested, with a maximum resolution bound by the average distance between detectable tag differences, and the number of array elements. Bulk testing of recombinants can be examined by pooling the tags from, for instance, five recombinant lines tested earlier on an individual basis and hybridizing the recombinant tag mixture to an array with the FRT 82 parental in the other channel, and another array with the rucuca parental in the other channel.

VI. Extension from Mismatched Restriction Sites for Polymorphism Discovery and Mapping Another method is provide, which also depends on detection of differential restriction enzyme digestion patterns; it thus shares some conceptual underpinnings with the method provided above. The procedure again depends on the fact that a nucleotide polymorphism in a restriction enzyme cut site will prevent that site from being digestion. One representative specific embodiment of this procedure is as follows:

1) Digest the genomic DNA of two individuals or samples to be compared with a restriction enzyme that recognizes a 6-basepair sequence.
2) Isolate the digested DNA from each sample, then denature and mix the digested DNA from the two samples together.
3) The DNA from an individual with a SNP will not be cut at a particular site, but cut in the second individual (or vice versa). Therefore, some of the DNA in the region of a polymorphism will hybridize as two shorter fragments annealed to a longer, uncut fragment.
4) Extend fluorescent-dye attached (or otherwise labeled) nucleotides from one of the shorter fragments, using one individual's longer, uncut fragment as template.
5) Apply the resultant DNA material to a microarray and detect variation by identifying spotted material with high fluorescent signal; high fluorescence is indicative of the presence of a polymorphism.

As noted above, at least certain steps may be carried out in a different order during preparation of the tag fragments.

Figure 6:
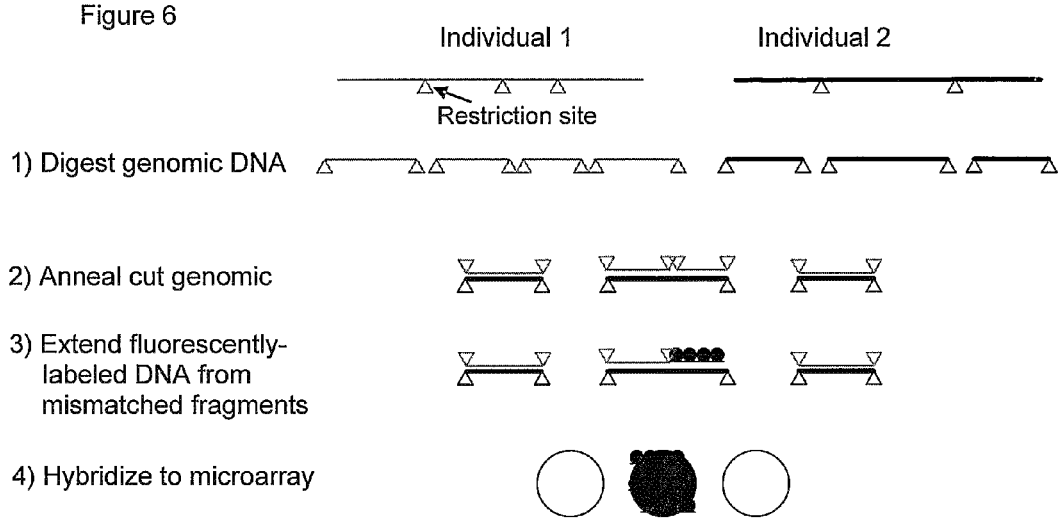
FIG. 6 is a schematic of a representative protocol to extend labeled nucleotides from mismatched restriction sites. The extra cut site in Individual 1 creates two DNA fragments that bind to a single longer fragment in Individual 2 (step 2, center). One of these shorter fragments acts as a primer for extension along the longer fragment template (from Individual 2). Fluorescently-labeled nucleotides are incorporated, allowing detection on, for instance, a microarray.

In this procedure, a polymorphism is detected by the presence of a signal on the array (see FIG. 6). Thus, a representative array analysis would have sample from a recombinant line annealed to sample form a parental line in one fluorescent channel, and sample from the two parentals annealed in another. The two parental lines annealed would produce signal at all loci containing a polymorphism in one parent and not the other. The recombinant annealed to one parental would produce a signal at all polymorphisms between the two as well; however, this would be restricted to the chromosomal regions where the recombinant line contains material from the other parent. Thus, the two parental lines annealed act as a source of SNP discovery, while the other fluorescent channel (recombinant annealed to parental) provides a way to map the areas matching the annealed parental.

For detection of fluorescent-labeled material extended from restriction site mismatch, the microarray options such as those described above are possible for this technique. The resolution of this approach is similar to the calculations of methods in Section V. A distinguishing feature is that the approach above produced signal at every cut site, whereas this approach produces a signal only where a SNP in one genome disrupts a cut site present in the other. Thus, multiple detected SNPs hybridizing to a single array element are much less likely in this approach. This frees the technique to be used with restriction enzymes cutting more frequently. For example, a restriction enzyme recognizing a four-basepair site will cut on average every 256 basepairs. In the method of Section V, this would create 12 independent sources of hybridizable material for each 3 kb genomic clone spotted on an array. For the current method, only a small subset of the sites would contain a polymorphism and a source of fluorescence. For example, a polymorphism rate of 1 in 100 would modify one in twenty-five four cutter sites. Twenty-five 4-cutter sites would on average exist at every 6,400 basepairs, so only half of the 3 kb genomic clones would contain a signal, and a smaller portion would have multiple signals.

It may be beneficial to compare this procedure to the procedure described in Section V, by repeating the detection of SNPs between the FRT 82 and rucuca lines for the 6-cutter and 5-cutter restriction enzymes previously used. The SNPs detected by one method can be compared with SNPs detected by the other. Loci containing probable SNPs by this method that were not scored by the above method can be isolated by PCR from, for instance, the parental and recombinant lines and sequenced to determine which method correctly identified the SNP.

Because this procedure only creates a signal on the array when a SNP is present, it is feasible to use restriction enzymes that cut at four-basepair recognition sites. Therefore, this class of enzymes can be used for SNP detection in the recombinant lines already used for the 5- and 6-cutter enzymes, described herein. It is noted that there are different technical issues that may arise using the greater SNP-detecting power of 4-cutter enzymes. For instance, the labeled fragment extends to the next restriction site by this method, so a 6-cutter digestion will create several thousand nucleotides of fluorescently-incorporated nucleotides, while a 4-cutter digestion is expected to only label several hundred nucleotides. Thus, producing a significantly intense hybridization to an array element may be more difficult with 4-cutter fragments than with 6-cutter fragments. Optionally, additional measures can be taken to increase signal intensity. By way of example, amino allyl incorporation followed by fluorescent dye attachment may be used to achieve greater efficiency of fluorescent dye incorporation. Alternatively, biotin-linked nucleotides can be incorporated, followed by streptavidin amplification of dye incorporation, to also increase fluorescence. The biotin could also allow purification of extension regions, which could be followed by addition of linkers for, e.g., cRNA or PCR amplification (or other analysis or processing) of the regions of interest.

VII. Restriction Site Tag Microarrays and Other Detection Methods

As discussed in Section V above, there are many options available for detection of tag differences using the differential RE tag detection methods or the detection of restriction site mismatch extension methods described herein. Most of these options are already available for any organism for which genomic approaches are used, such as cDNA arrays or arrays of long oligos. Arrays of restriction site tags are specifically provided herein. If a goal of a project is to map traits via SNPs, for instance, then such an array make particular sense, as they allow for higher resolution mapping than a microarray created for expression studies with the same number of array elements.

A genomic tag array consists of DNA flanking each site of digestion for a particular restriction enzyme in the genome. Thus, when the experimental and array restriction sites match, each element of the array is capable of detecting a restriction site tag, or an extension from restriction site polymorphism. By way of example, a genomic restriction site tag microarray can be generated using the following procedure:
1) Shear genomic DNA to fragments 3-5 kb in length.
2) Digest the sheared DNA with a restriction enzyme, producing a fragment with a restriction site at one end and blunt on the other.
3) Isolate DNA fragments 1 kb in length.
4) Ligate DNA fragments into a plasmid vector
5) Transform bacteria with plasmids.
6) Pick individual colonies.
7) Amplify inserts.
8) Spot onto array.

As noted above, certain steps may be carried out in a different order than is listed. For instance, shearing and restricting the genomic DNA may be carried out in either order.

With regard to ligating the DNA fragments into the plasmid vector, it will be appreciated that different cloning schemes could be used. By way of example, it is specifically contemplated to digest the vector with the original RE used to generate the fragments, plus a blunt cutter RE. In this procedure, the fragment will readily ligate to the non-blunt side, and the subsequent forced spatial localization of the blunt end to the area around the vector will increase the ligation of that side.

Restriction tag arrays have several advantages for detecting polymorphisms, such as SNPs. First, unlike spotted long oligonucleotide or cDNA arrays, this array would contain hybridizable material at every element when the array restriction enzyme used is matched with the experimental restriction enzyme. A typical cDNA array element would only have a ~50% chance of containing DNA matching a particular tag, and a long oligonucleotide array even less. Thus, the restriction tag array will maximize the number of polymorphisms detected.

For organisms with a genome where the sequence is not known, cDNA arrays have been the only other option in the past. However, the genomic tag array is more efficient in that there is less of a chance of over-sampling one locus, compared to cDNA arrays that may have heavy representation of a few highly transcribed genes. The genomic tag array also samples the more highly polymorphic intergenic as well as gene region DNA, increasing the number of polymorphisms/ SNPs detected compared to a cDNA array.

If SNPs are discovered, particularly using the procedures provided in Section V, then the length of the spotted elements on the analysis array (of whatever type) can be important. Array elements containing nucleic acid sequences that are too long will be hybridized to by multiple restriction site tags, making interpretation of the results less certain. The average length of cDNAs or the 3 kb clones use herein for the working example genomic array makes a 6-cutter enzyme most likely to obtain clear results. The shorter length of DNA spotted onto the genomic tag array as described herein allows for restriction enzymes that cut more frequently, such as those that recognize a 5 basepair sequence. Whereas in an individual polymorphic at a rate of 1 nucleotide in 100, a SNP altering a restriction site would occur every (4000 bp*100/6) or 66 kb for a six-cutter enzyme, a five-cutter enzyme would be polymorphic every (2000 bp*100/5) or 40 kb.

By way of example, a library of BamHI tags of 1 kb in length can be prepared from genomic DNA of the *Drosophila melanogaster* line FRT 82, commonly used for genetic screens. There are likely to be ~30,000 BamHI sites in the genome. In a first instance, about 13,000 restriction site tags could be amplified, for approximately ⅓ coverage of the genome, and these elements spotted on glass slides. These procedures are routine to those of ordinary skill in the art.

The genomic tag arrays can be employed in the protocols described herein. The restriction site tag approach can be examined, for instance, by isolating BamHI tags from FRT 82 flies, rucuca flies (often used for mapping by recombination), and a recombinant fly line containing a mixture of rucuca and FRT 82 chromosomal material. One array is hybridized with FRT 82 tags versus rucuca tags; a second array is hybridized with FRT 82 tags versus recombinant tags, and a third array with rucuca tags versus recombinant tags. The first array allows discovery of all detectable SNPs between the FRT 82 and rucuca chromosomes. The second and third arrays should show tag differences in the areas where the recombinant line does not match chromosomes material with the parental line being co-hybridized. These arrays are therefore expected to have a subset of SNPs compared to the first array, and the second and third should have complementary patterns of detectable tag differences. Because the genomic tag array will have a random set of clones, spot identity is established after the experimental data is collected, for instance by sequencing (e.g., pyrosequencing) of clones of interest to place them in the genome.

Although a genomic tag array is optimized for experiments using genomic tags created with the same restriction enzyme used to create the array, other restriction enzyme tags can also be used to increase the number of SNPs detected. The mapping procedures can be repeated using tags isolated with other restriction enzymes. By way of example, 6-, 5- and 4-cutter enzymes can be used to create tags. The number of SNPs detected with each restriction enzyme for that specific genome can then be determined.

It is expected that 5-cutter tags will be present once per array element (where the array elements are about 1500 to 3000 bp), while 4-cutter tags will have multiple instances per element, and therefore complicate interpretation of the results. In those instances where a fractional decrease in array element hybridization is consistently interpretable, then the use of 4-cutter enzymes will increase the resolution of the array even more. Even without the use of 4-cutters, the ability to query different SNPs with each restriction enzyme used is believed to allow for maps of higher resolution, and provide independent confirmation of predicted regions containing mutations.

The genomic tag microarrays provided herein can map SNPs at a resolution which is limited by the number of array elements on the microarray. The resolution of a microarray with 10,000 unique tags can be no greater than 12 kb between detectable SNPs (the 120 million basepairs in the *Drosophila* genome divided by 10,000 elements, for instance). To achieve this resolution requires multiple procedures with different restriction enzymes (for instance, twenty experiments involving 6-cutter enzymes, fewer experiments if 4- or 5-cutters are used). While this resolution would be adequate for mapping a mutation produced by a genetic screen in the fly, this number of elements would produce lower resolution SNP maps in organisms with larger genomes, although gene densities decrease as genome size increases. Obviously, more elements could be added to the array. However, most spotting array printers produce arrays with a maximum of 35,000 elements. Commercial arrays involving synthesis of oligos in situ can produce several hundred thousand elements per array.

One low-cost and rapid method to map SNPs at a higher resolution would be to do use a 10,000 element array to identify a region of interest, then produce a high resolution array of that smaller region. For instance, if the initial array analyses mapped a mutation to a 300 kb region, then genomic tags could be isolated from BACs spanning that region. Only a few hundred tags would be needed to have 95% of all 6-cutter sites from a single digest, so a reasonable strategy would be to isolate 200 tags each from two different restriction enzyme digestions. The creation of a mini-array of this type would take no more than a few weeks and a few hundred dollars. The same material used to roughly map the mutation to that region could then be hybridized to the mini-array to create a very high-resolution map of the region.

By way of example, a high-resolution genomic tag array of a 300 kb region between ebony (e) and claret (ca), two visible markers on the rucuca $3^{rd}$ chromosome, can be generated. Restriction tags generated after BamHI digestion of the two BACs that span this region (of which there are 384) can be generated and spotted onto glass slides. The 384 tags are expected oversample most BamHI sites in the BACs, and 90% of the sites are expected to have at least one tag. Thus, the resolution of SNPs detected should improve, as more sites in the region are detectable on the array. Genomic tags from recombinant lines thought to have breakpoints in the region can be hybridized to this mini-array and the increase in SNP detection assessed.

Non-array based strategies may be even more rapid at the scale of detecting tags from, for instance, a few hundred kilobases. At larger scales, the number of tags needed to be sequenced makes the cost prohibitive. There are currently methods to purify genomic DNA from a particular region, based on the hybridization of total genomic DNA to bead-bound BAC DNA (Bashiardes et al., *Nature Methods* 2:63-69, 2005). Thus, tags from the region of interest can be isolated, and individual tags sequenced. If particular tags were missing from one individual, then that would indicate the presence of a SNP at that site. Multiple options exist for rapid and/or low-cost sequencing, from pyrosequencing of individual tags (Ramon et al., *J. Translat. Med.* 1(9), p 1-10, Epub 26 Nov. 2003), to SAGE-type strategies for sequencing of concatamers (Wang et al., *Proc Natl Acad Sci USA* 99(25): 16156-61, 2002; Epub 2 Dec. 2002); for a review of "fast" sequencing technologies, see Bonetta, *Nature Methods* 3(2): 141-147, 2006. For projects where multiple regions may be of interest, such as mapping mutations from a genetic screen, rapid sequencing-based approaches may be most efficient. By way of example, genomic DNA of the two lines discussed above can be isolated by purification on a single BAC, and pyrosequencing analysis applied to the 384 tags from each line. Using these analyses, it can be determined if tag quantity in a particular situation can reliably indicate the presence or absence of restriction sites in the recombinants.

It is further recognized that any short nucleotide tags associated with restriction sites, as produced by the methods described, can be assayed or examined using platforms other than competitive hybridization to microarrays. By way of non-limiting example, two methods are described further below: tag-specific amplification and bead-based hybridization detection. One of ordinary skill in the art will recognize that additional methods can be used, based on the teachings provided herein. For instance, high throughput analysis using a microfluidic system is another option. By way of example, the following publications provide descriptions of various microfluidic systems useful for analysis of biomolecules including nucleic acids, and other systems will be recognized by those of ordinary skill in the art: Olsen et al., *Anal. Chem.* 74:1436-1441, 2002; Wei et al., Nucleic Acids Res. 33:e78, 2005; US 2005/0221373; US 2005/0053952; US 2005/0032076; US 2003/0032035; US 2003/0165964; and US 2004/0110208

Once the presence of a tag has been determined as polymorphic between two individual samples, one exemplary and non-limiting application of that information is to assay the presence (or absence) of that tag in different individuals or populations. A particular situation where this would be useful, for instance, is after a chromosomal region has been identified as potentially linked to a trait. Individual polymorphic markers within that region can then be assayed in bulk population samples to detect low frequency polymorphism states in the population. The presence of a tag inherited from a parent without the trait would allow that portion of the (potentially) linked region to be ruled out as containing the gene (more generally, sequence) of interest. Isolation of the DNA surrounding a restriction site allows this detection to be carried out by the following exemplary method:
1) Identify tags as polymorphic between two populations as described herein (e.g., by array or other detection method).
2) Identify a tag of interest by selecting a polymorphic spot mapping within the chromosomal region of interest and showing the presence of a tag in the population not having the trait of interest.
3) Design amplification primers, one of which is specific for the sequence of the tag of interest, the other corresponding to sequence in a DNA adapter sequence (e.g., a relatively short nucleic acid, such as a linker, part of which complements the overhanging nucleotide sequence of the restriction site used in generating the tag and which includes a sequence to which an amplification primer can bind) ligated to the restriction site.
4) Isolate tags from a bulk population that exhibits (at some level) the trait of interest.
5) Amplify (e.g., using PCR or another amplification technique) the isolated tags using the amplification primers.

If the tag of interest is amplified from the bulk population, it indicates that at least some individuals within that population inherited DNA from a parent(s) without the trait, and therefore the trait cannot be at the locus of the tag. By repeated sampling of potential tags of interest, the exact region always inherited from the parent with the trait can be determined.

The described PCR-based detection method results in an amplified DNA fragment of known size (known from the location of the restriction site and the chosen primer site within the tag). The presence (or absence) of amplified material can be detect by running the product of the PCR reaction through an agarose gel and visually inspecting it for a band of the predicted size, or by other art recognized methods.

Another representative method is a bead-based high-throughput system for detecting polymorphic markers after tag isolation. PCR amplification within oil droplets (emulsion PCR) on a bead-capture system has recently been used to successfully create beads covered with millions of copies of a short stretch of DNA (Margulies et al., *Nature* 437(7057): 376-80, 2005; Epub Jul. 31, 2005). See also U.S. Patent Publication 2005/0079510, which describes methods for carrying out bead emulsion nucleic acid amplification to produce beads each of which is covered with a highly amplified sequence. Each of these beads can be conceptually treated as though it is an array element, with the difference being that the DNA is not spotted on a solid glass slide or other contiguous surface, but instead the DNA is adhered to a bead in liquid suspension.

DNA from any source can be used for making a bead library—sheared genomic DNA, the isolated tags or cDNAs, for example. The tags isolated from two individuals or two populations, for instance, can be hybridized to the bead suspension, after fluorescent labeling of tags (which allows their origin to be distinguished). As for read-out analysis by an array or microarray, there will be beads with no signal from either source of tags if the DNA amplified on the bead is not near a restriction site; there will be beads that have equal amounts of label (such as fluorescent label; Cy3 and Cy5 dyes, for example), suggesting that a restriction site is present in both tag sources in the DNA amplified on that bead; and there will be beads with fluorescent label from a single source (Cy3 dye or Cy5 dye, for example), suggesting that the DNA amplified on the bead has a restriction site in one tag source but not the other. Similarly, when assaying the presence of tags in a bulked population, there will be beads with varying relative amounts of Cy3 and Cy5 dyes, indicating the relative proportion of individuals in those populations with the particular polymorphic tag hybridized to the DNA carried by the bead. An advantage of a bead-based system is that the number of possible tags assayed is not limited by the number of spots on the array, and will most likely saturate all possible polymorphic tags between the individuals or populations.

Beads with differential fluorescent intensities can be identified and selected (for instance, selected for further analysis) by a variety of methods, including sorting by fluorescence activated cell sorting (FACS) (Mastrobattista et al., *Chem. Biol.* 12(12): 1291-1300, 2005). After hybridization of tags to bead DNA, the hybridized beads can be re-packaged in oil droplets to allow sorting by FACS machine. Individual beads are rapidly sorted by fluorescent signal into different capture bins by FACS, allowing the selection of beads with very high Cy3 or Cy5 fluorescent signals (or any other differential fluorescence or other tag signals).

Whereas an array-based system makes identification of individual array elements possible by tracking and/or sequencing the template of the individual amplification reactions, a bead-based system requires bead DNA identification for every test. Although multiple methods are possible, one example useful for such identification is sequencing of high-intensity bead DNA for identification. After sorting by FACS, bead DNA can be diluted and PCR amplified for sequencing. See also published U.S. patent documents US 2002/0094116 and US 2006/0029267, for methods of reading reporter labeled beads.

Once beads with differential signal have been sorted, DNA is released from the beads into individual containers (such as wells in a microtiter plate), and amplification and sequencing of individual samples can be carried out. The sequences that result would identify those tags that had been selected by the FACS. The selected sequences could then be mapped to a known genomic sequence, or used to design primers for amplification of BAC libraries or other genomic resources, for instance.

If high numbers of bead identifications are desired, a serial analysis of gene expression (SAGE)-like approach can be utilized to sequence multiple short representations of the DNA available in the selected beads. Beads can also be used as a source for array element generation, allowing the selection of highly polymorphic elements prior to laborious amplification.

VIII. Subtracted Restriction Site Tag Microarrays and Libraries

As described above, genomic tag arrays and bead libraries consist of DNA flanking sites of digestion for a particular restriction enzyme in the genome. A very efficient array (or set/library of nucleic acid-loaded beads) would contain only elements that differ between individuals. This is possible if the tags from the two individuals undergo a round of subtractive hybridization, a procedure that removes DNA in common. Thus, a 5000 element array (or other collection of nucleic acid elements) could assay 5000 SNP differences between individuals. The creation of a genomic restriction site tag microarray would use the following procedure:
1) Shear genomic DNA to fragments 3-5 kb in length.
2) Digest the sheared DNA with a restriction enzyme, producing a fragment with a restriction site at one end and blunt on the other.
3) Isolate DNA fragments 1 kb in length.
4) Perform subtractive hybridization between the two tag sets.
5) Ligate DNA fragments into a plasmid vector.
6) Transform bacteria with plasmids.
7) Pick individual colonies.
8) Amplify inserts.
9) Spot onto array.

As noted with other methods described herein, certain steps may be carried out in a different order than is listed. For instance, shearing and restricting the genomic DNA may be carried out in either order.

Subtracted tag arrays can be used, for instance, in the ways described above for use with non-subtracted genomic tag arrays. By way of example, subtractive hybridization arrays can be generated for any particular species. In one particular embodiment, subtractive arrays can be generated from oceanic and lake forms of stickleback. Such an array could then be used to map differences between these stickleback variants, for instance to map armor loss differences between these populations.

Similarly, subtracted tag bead libraries and otherwise formatted collections of subtracted nucleic acids can be produced and used.

IX. Computer Assisted (Automated) Detection and Analysis

The data generated by assaying the disclosed arrays or other collections of nucleic acids can be analyzed using known computerized systems. For instance, an array or collection can be read by a computerized "reader" or scanner adapted for the analysis of the format of the array or collection, and quantification of the binding of target to individual addresses (features) carried out using computer algorithms. Likewise, where a control target has been used, computer algorithms can be used to normalize the hybridization signals in the different features. Such analyses can be referred to as "automated detection," in that the data is being gathered by an automated reader system.

In the case of labels that emit detectable electromagnetic wave or particles, the emitted light (e.g., fluorescence or luminescence) or radioactivity can be detected by very sensitive cameras, confocal scanners, image analysis devices, radioactive film or a phosphorimager, which capture the signals (such as a color image) from the array (or other signal source). A computer with image analysis software detects this image, and analyzes the intensity of the signal for each probe location in the array. Signals can be compared between spots on a single array, or between arrays (such as a single array that is sequentially interrogated with multiple different target molecule preparations), or between the labels of different targets (or combinations of targets) on a single array.

Computer algorithms can also be used for comparison between spots on a single array or on multiple arrays. In addition, the data from an array can be stored in a computer readable form.

Certain examples of automated array readers (scanners) will be controlled by a computer and software programmed to direct the individual components of the reader (e.g., mechanical components such as motors, analysis components such as signal interpretation and background subtraction). Optionally software may also be provided to control a graphic user interface and one or more systems for sorting, categorizing, storing, analyzing, or otherwise processing the data output of the reader.

To "read" an array, an array that has been assayed with a detectable target to produce binding (e.g., a binding pattern) can be placed into (or onto, or below, etc., depending on the location of the detector system) the reader and a detectable signal indicative of target binding detected by the reader. Those addresses at which the target has bound to an immobilized nucleic acid mixture provide a detectable signal, e.g., in the form of electromagnetic radiation. These detectable signals could be associated with an address identifier signal, identifying the site of the "positive" hybridized spot. The reader gathers information from each of the addresses, associates it with the address identifier signal, and recognizes addresses with a detectable signal as distinct from those not producing such a signal. Certain readers are also capable of detecting intermediate levels of signal, between no signal at all and a high signal, such that quantification of signals at individual addresses is enabled.

Certain readers that can be used to collect data from the arrays, especially those that have been interrogated using a fluorescently tagged molecule, will include a light source for optical radiation emission. The wavelength of the excitation light will usually be in the UV or visible range, but in some situations may be extended into the infra-red range. A beam splitter can direct the reader-emitted excitation beam into the object lens, which for instance may be mounted such that it can move in the x, y and z directions in relation to the surface of the array substrate. The objective lens focuses the excitation light onto the array, and more particularly onto the (polypeptide) targets on the array. Light at longer wavelengths than the excitation light is emitted from addresses on the array that contain fluorescently labeled target molecules (i.e., those addresses containing a nucleic acid molecule within a spot containing a nucleic acid molecule to which the target binds).

In certain embodiments, the array may be movably disposed within the reader as it is being read, such that the array itself moves (for instance, rotates) while the reader detects information from each address. Alternatively, the array may be stationary within the reader while the reader detection system moves across or above or around the array to detect information from the addresses of the array. Specific movable-format array readers are known and described, for instance in U.S. Pat. No. 5,922,617, hereby incorporated in its entirety by reference. Examples of methods for generating optical data storage focusing and tracking signals are also known (see, for example, U.S. Pat. No. 5,461,599, hereby incorporated in its entirety by reference).

For the electronics and computer control, a detector (e.g., a photomultiplier tube, avalanche detector, Si diode, or other detector having a high quantum efficiency and low noise) converts the optical radiation into an electronic signal. An op-amp first amplifies the detected signal and then an analog-to-digital converter digitizes the signal into binary numbers, which are then collected by a computer.

In embodiments that employ bead-based collections of nucleic acids for read-out, beads with differential fluorescent intensities can be identified and selected by a variety of methods, including sorting by fluorescence activated cell sorting (FACS) (Mastrobattista et al., *Chem Biol.* 12(12):1291-1300, 2005). See also published U.S. patent documents US 2002/0094116 and US 2006/0029267, for methods of reading reporter labeled beads.

X. Polymorphism Detection Kits

Polymorphism (or variant) detection arrays or collections of tags (for instance, tag sequences immobilized on beads or other non-array based collections) as disclosed herein can be supplied in the form of a kit for use in nucleic acid analyses. In such a kit, at least one array (or other collection) is provided. The kit also includes instructions, usually written instructions, to assist the user in probing the array or collection. Such instructions can optionally be provided on a computer readable medium.

Kits may additionally include one or more buffers for use during assay of the provided array or collection. For instance, such buffers may include a low stringency wash, a high stringency wash, and/or a stripping solution useful with array analysis. These buffers may be provided in bulk, where each container of buffer is large enough to hold sufficient buffer for several probing or washing or stripping procedures. Alternatively, the buffers can be provided in pre-measured aliquots, which would be tailored to the size and style of array included in the kit. Kits for use with bead-based collections also may be provided with reagents or buffers useful in carrying out hybridization reactions on the beads, as well as components useful in analysis or "reading" of the hybridized beads.

Certain kits may also provide one or more containers in which to carry out array-assaying reactions.

Kits may in addition include either labeled or unlabeled control target molecules. Such molecules can be provided to provide for internal tests of the labeling procedure or interrogation of the array or other nucleic acid collection, or both. The control target molecules may be provided suspended in an aqueous solution or as a freeze-dried or lyophilized powder, for instance. The container(s) in which the controls are supplied can be any conventional container that is capable of holding the supplied form, for instance, microfuge tubes, ampoules, or bottles. In some applications, control probes may be provided in pre-measured single use amounts in individual, typically disposable, tubes, or equivalent containers.

Specific examples of target molecules include preparations of nucleic acids that correspond to the sequences used to construct the array or non-array based collection provided in the kit. Other control targets may be targets that comprise one or more previously identified variants for the sequence(s), such that the user is provided with a non-consensus control "test" sample.

The amount of each control target supplied in the kit can be any particular amount, depending for instance on the market to which the product is directed. For instance, if the kit is adapted for research or clinical use, sufficient control target(s) likely will be provided to perform several controlled analyses of the array. Likewise, where multiple control targets are provided in one kit, the specific targets provided will be tailored to the market and the accompanying kit.

In some embodiments, kits may also include the reagents necessary to carry out one or more target-labeling reactions. The specific reagents included will be chosen in order to satisfy the end user's needs, depending on the type of target molecule (e.g., DNA or RNA or PNA or some other derivative) and the method of labeling (e.g., radiolabel incorporated during target synthesis, attachable fluorescent tag, element of a strept/avidin:biotin system, etc.).

Further kits are provided for the labeling of target molecules for use in assaying arrays or provided herein. Such kits may optionally include an array or collection to be assayed by the so labeled target molecules. Other components of the kit are largely as described above for kits for the assaying of arrays and other collections.

The following examples are provided to illustrate certain particular features and/or embodiments. These examples should not be construed to limit the invention to the particular features or embodiments described.

EXAMPLES

Example 1

Use of Restriction Site Tags for Single Nucleotide Polymorphism (SNP) Discovery and Mutation Mapping This example provides representative methods for generating restriction site tags and their use in detection of polymorphisms. A schematic overview of the exemplary method is provided in FIG. 1.

Methods

Digestion of Genomic DNA

Genomic DNA was prepared using standard techniques. (Since the DNA preparation is to be sheared, even relatively poor or degraded genomic samples are satisfactory.) The genomic DNA preparation was then cut with a 6-cutter restriction endonuclease, EcoRI in the current instance, though others are contemplated. 10 μg of clean, non-degraded genomic DNA from rucuca and FRT82 flies was brought to 175 μl with dH$_2$O. To this, 20 μl of 10×6-cutter buffer (in this case, EcoRI buffer) was added and the tube flicked gently to mix. The reaction mixture was brought to the bottom of the tube by briefly spinning in a microfuge. A 5 μl aliquot of 6-cutter enzyme (EcoRI in this case) was added, and the tube flicked gently to mix, then spun down again. The reaction was incubate at 37° C. for 3 hours, though other times (e.g., about 3-5 hours) could be used. The resultant digest was analyzed by running 2.5 µl on a 1% agarose gel; digestion is illustrated by a DNA smear down.

The digested DNA was extracted using phenol/chloroform, ethanol precipitated with glycogen, and the resultant pellet resuspended in 20 µl low TE (10 mM Tris pH 8.0, 0.1 mM EDTA).

Biotin Linker for EcoRI

Biotin oligos were from Integrated DNA Technologies. The Biotin Linker specific for an EcoRI digestion was made from the following two synthetic oligos:

```
                                              (SEQ ID NO: 1)
5'-Biotin- TTT CGA CGC TCG CAT CTG GAC AGG-3'

(SEQ ID NO: 2)
5'-Phosphate- AAT TCC TGT CCA GAT GCG AGC GTC G-3'
```

The oligonucleotides were allowed to anneal to each other to form Biotin Linker for EcoRI restriction enzyme. One of ordinary skill in the art will appreciate how to readily vary the sequence of these specific oligonucleotides in order to generate Biotin Linkers for use with other restriction enzymes.

Ligate Biotin Linkers onto Sticky Ends of Digested Genomic DNA

To the 20 µl sample of restriction digested genomic DNA produced above, 5.5 µl (10 µM) of Biotin Linker (specific to the used 6-cutter) was added, along with 3 µl 10× T4 ligase buffer w/ ATP. The tube was flicked gently to mix, and the sample spun to the bottom of the tube. The reaction was incubated at 50° C. for 2 minutes, let sit at room temperature (RT; approximate 22° C.) for 10 minutes, and 1.5 µl T4 ligase High-Concentration (NEB) added. The tube was flicked gently to mix, the sample spun to the bottom, and incubated at RT for 2-3 hours. The resultant preparation was analyzed by running 2.5 µl on a 1% agarose gel next to diluted biotin linker; free linkers will ligate to themselves and thereby run slower than the unligated, diluted biotin linker.

Gel Extract Genomic DNA Away from Free Linkers

Biotinilyated sample prepared as above was run for a short time (~20 minutes at ~75V) on a 2% TAE low-melt agarose gel, and the highest molecular weight (top) band comprising the digested genomic DNA with incorporated linkers) was cut out. Care was taken not to harvest the "bottom band" (unincorporated linkers) from the gel. The prepared DNA was recovered from the low melt agarose using a GELase™ Agarose Gel-Digesting Preparation kit, following the manufacturer's protocol (Epicentre Biotechnologies, Madison, Wis.). The DNA was resuspended in 40 µl TE. The resultant preparation was analyzed by running 2.5 µl on a 1% agarose gel; correct product is illustrated by a DNA smear down.

Sonication of Linker-Incorporated Digested Genomic DNA

Gel extracted, digested and Tinkered DNA prepared as above was brought up to a final sample volume of 200 µl with TE, and sonicated using a using Branson Sonicator 450 (Duty Cycle—80, Output—1.2) as follows: 10 pulses, quick spin, 1 minute on ice; repeat 10 times. The resultant, sheared DNA preparation was ethanol precipitated with glycogen, and the pellet resuspended in 40 µl low TE. A 2.5 µl aliquot was run out on a 2% agarose gel to confirm the sonication; the majority of the DNA is sheared to ~200-600 bp when the sonication has been successful.

Pulldown Biotin End-Linked Genomic DNA

The sample was brought to 100 µl with low TE, and reserved while the beads were prepared. Streptavidin Dynabead solution (50 µl; Dynal Biotech, Brown Deer, Wis.) was placed into a separate 1.5 ml tube, to which was added 150 µl 2× B/W solution (10 mmol/L Tris-HCl, 2 mol/L NaCl, 1 mmol/L EDTA, 1 mL/L Tween 20, pH 7.6). This was pipetted up and down to mix. A magnet was used to immobilize the beads, and the supernatant removed. The beads were washed with 200 µl 2× B/W by pipetting up and down, and the wash supernatant removed after the beads were immobilized with a magnet. The beads were resuspended in 100 µl 2× B/W, and the 100 µl sample added and mixed gently by pipetting up and down. This was incubated for 15-20 minutes at RT, mixed intermittently by pipetting up and down. The beads were immobilized with a magnet, the supernatant removed, and the wash procedure repeated three times with 1× B/W. The beads were washed once more with 200 µl, then with 200 µl low TE. The 200 µl TE wash supernatant was saved to be used as a carryover control. After the washing regimen, the beads were resuspended in 85 µl low TE.

Release Genomic DNA Using A 6-Cutter Restriction Endonuclease

To release the prepared tag fragments from the Dynabeads, the DNA was digested using the same restriction enzyme used to generate the fragments, as follows. To the 85 µl sample, 10 µl of 10× 6-cutter buffer (in this case, EcoRI) was added and mixed by pipetting up and down. A 5 µl aliquot of the 6-cutter enzyme (here, EcoRI) was added and mixed in by pipetting up and down. The mixture was incubated at 37° C. for 1 hour, mixing every 10 minutes by pipetting up and down. A magnet was used to immobilize the now-stripped beads, and the supernatant (containing the prepared DNA tag fragments) removed and placed into a new 1.5 µl tube; the beads were discarded. The DNA preparation was cleaned by phenol/chloroform extraction. By way of example, the following protocol has been used:

Phenol/Chloroform Extraction

Sample volume was brought to 200 µl w/ TE

150 µl Phenol and 150 µl Chloroform were added

This was inverted several time, and vortexed well

Phases were separated by spinning in a microcentrifuge at max speed for 2 minutes The top (aqueous) layer was transferred (~220 µl) to new tube 200 µl Chloroform was added This was inverted several time, and vortexed well Phases were separated by spinning in a microcentrifuge at max speed for 2 minutes The top (aqueous) layer (~200 µl) was transferred to new tube From this point forward, both the sample ("pulldown") and the low TE wash control were processed. The samples were precipitated with ethanol and glycogen. By way of example, the following protocol has been used:

EtOH Precipitation w/ Glycogen

The volume of sample to be precipitated was noted

1/10 noted volume of 3M NaOAc (pH 7.0) was added

The tube was flicked to mix, then the sample brought to the bottom of the tube with a quick microfuge spin 3 µl per 200 µl of sample of 20 µg/µl Glycogen was added The tube was flicked to mix, then the sample brought to the bottom of the tube 2.5× noted volume of ice cold 100% EtOH (ethanol) as added The tube was inverted several time to mix, then placed at −80° C. for 30 minutes DNA was pelleted by spinning at max speed for 15 minutes at 4° C.

The supernatant was removed, the sample spun briefly again, and any remaining supernatant removed The pellet was washed by adding 1 ml 75% Ice Cold EtOH, vortex until pellet dislodges from the tube DNA was pelleted by spinning at max speed for 5 minutes at 4° C.

The supernatant was removed, the sample spun briefly again, and any remaining supernatant removed The pellet was allowed to air dry for ~5 minutes The resultant pellets resuspended separately in 20 µl TE. 2.5 µl aliquots of each were run out on a 1% agarose gel for a short time; DNA was lightly visible in the pulldown sample, but nothing should be seen in the carryover control.

Random Amplification of Pulldown

The DNA samples were labeled using standard techniques. The following is a representative protocol:

First, the ends of the DNA preparation were repaired. The sample was brought to 43 µl in dH$_2$O in a 1.5 ml tube. To this was added 1 µl (10 mM) dNTPs, 5 µl 10× EcoPol buffer, and 1 µl Klenow exo+ (NEB; Beverly, Mass.). The mixture was incubated at 37° C. for 30 minutes, then placed at 75° C. for 10 minutes. The reaction was then purified using a Qiagen PCR Purification Kit, eluted in 30 µl EB (provided by the manufacturer).

Blunt-end linkers for use with random amplification were generated by annealing the following oligonucleotides (Integrated DNA Technologies, Coralville, Iowa):

```
                                            (SEQ ID NO: 3)
5'- CTG CTC GAA TTC AAG CTT CT-3'

(SEQ ID NO: 4)
5'-Phosphate- TCG AGC TGT CCA GAT GCG AGC GTC G-3'
```

The resultant double-stranded blunt-end linkers were added to the resultant fragment preparations as follows: 3.5 µl of dH$_2$O was placed into a micro-tube, to which was added 2 µl of end-repaired sample (prepared as above), 2 µl (1 µM) blunt-end linker, 2 µl 10× T4 Ligase buffer w/ ATP, and 0.5 µl T4 Ligase (High-Concentration, NEB). This mixture was incubated at Back-RT (~18° C.) for 2-3 hours.

The blunted ended sample was then amplified using PCR. By way of example, the following reaction mixture has been used, in a 1.5 ml tube:

38.5 µl dH$_2$O
5 µl Thermo Pol buffer
1 µl (10 mM) dNTPs
0.5 µl NEB Taq
2 µl 20 µM Primer (SEQ ID NO: 3)
3 µl ligated sample (prepared as above)

Amplification was carried out in a thermocycler, using the following program cycle[]AMPC: 95° C. for 5 minutes; repeat for 20 cycles 90° C. for 45 seconds, 48° C. for 45 seconds, 72° C. for 3 minutes; 72° C. for 5 minutes; 4° C. to stop and store. The resultant amplification product was purified using a Qiagen PCR Purification Kit, eluted in 30 µl EB. A 2.5 µl aliquot was run out on a 2% agarose gel; the majority of the DNA should be ~200-600 bp. The concentration of the DNA preparation was now determined using a spectrophotometer. Preparations usually yielded around 2-4 µg.

Alternatively, amplification could be performed substantially as described in Malrigiorgos et al. (*Nature Biotechnology* 20:936-939, 2002), or other methods that will be known to those of ordinary skill in the art.

Genomic Labeling and Hybridization

Samples to be run against each other on an array are labeled, for instance using the following procedures. By way of example, one sample was labeled with Cy3 and the other with Cy5, though one of ordinary skill in the art will recognize that other dye pairs (or labeling systems) could be used.

For each labeling, 0.5 µg of DNA prepared as above was brought to a volume of 10.5 µl w/ dH$_2$O. To this was added 10 µl 2.5× random primer mix (BioPrime Array CGH Purification module, Invitrogen, Carlsbad, Calif.), and the sample was mixed and spun down to the bottom of the tube. The reaction was denatured at 100° C. for 2 minutes, the sample spun back to the bottom of the tube, and placed on ice. To this was added:

2.5 µl 10× dCTP mix
1.5 µl Cy3 or Cy5
0.5 µl Klenow exo– (Hi-concentration)

The reaction was incubated at 37° c. for 2-5 hours.

The DNA was purified using Qiagen nucleotide removal kit. PN buffer (provided by the manufacturer) was added to each of the two labeling reaction samples, then mixed by pipetting. The two labeling reactions were then combined and applied to the Bioprime purification column from Invitrogen (Carlsbad, Calif.). The mixed labeled sample was then eluted in 40 µl EB buffer, and dried under vacuum.

The sample was resuspended in Hyb Mix; 35 µl was used for 22×60 mm lifterslips or 38 µl for 24×60 mm lifterslips, as follows:

Hyb Mixture (Per Slide):
For 22×60 Lifterslips
20 µl 100% Formamide
6 µl 20×SSC
4 µl 10% SDS
4 µl 50×Denhardt's
3.2 µl 10 mg/ml Salmon Sperm DNA
For 24×60 Lifterslips
40 µl 100% Formamide
12 µl 20×SSC
8 µl 10% SDS
8 µl 50×Denhardt's
6.4 µl 10 mg/ml Salmon Sperm DNA The samples (now referred to as probe) were denatured by incubation at 100° C. for 2 minutes, given a quick spin to settle the contents to the bottom of the tube, and pipetted onto the center of the lifterslip after waiting 30 seconds. The loaded lifterslip was immediately contacted with the slide. The slide and coverslip were then sealed in Hyb chamber (after placing 25 µl of 3×SSC in each end), and the hybridization carried out for 12-16 hours at 42° C.

Wash Protocol

Wash solutions #1, #2, and #3, made fresh for each experiment consisted of the following:

Wash #1: 380 ml dH$_2$O, 20 ml 20×SSC, 1.2 ml 10% SDS
Wash #2: 198 ml dH$_2$O, 2 ml 20×SSC
Wash #3: 200 ml dH$_2$O, 0.5 ml 20×SSC Wash solution #1 was poured into two slide chambers (one wide and one normal size), using 200 ml in each. Wash solutions #2 and #3 were each poured into a separate slide chamber (normal size). Slide racks were placed into the normal sized slide chamber containing wash solution #1 and into the slide chamber with #2

The Hyb chambers were disassembled and the slide were quickly submerged (keeping the coverslip face up) the wide sized slide chamber that contains wash solutions #1 but does not contain a slide rack. Once the slide was submerged, it was tilted to the side and the coverslip fell off immediately. The slide was then quickly transferred into the rack in wash solution #1. The slides were washed in each wash for 2 minutes, plunging up and down several times. Slides were transferred individually from wash solution #1 into #2; the whole rack (with the slides) was transferred from #2 to #3. When the slide rack was taken out of wash #3, it was immediately spun for 5 minutes at 600 rpm, then scanned using a GenePix 4000B Microarray Scanner from Axon Instruments (now part of Molecular Devices).

Results

This example demonstrates that the above protocols can be used to isolate genomic restriction site tags in a non-biased and reproducible manner. Genomic restriction site tags were prepared as described above from rucuca and FRT82 flies, using the restriction enzyme EcoRI. These tags were labeled with different fluorophores and applied to a microarray. The two independent trials give the same pattern of yellow (tags present in both genomes), black (tags present in neither genome), red (tags present in the rucuca genome only) and green (tags present in the FRT82 genome only). This demonstrates that the approach is robust enough to detect the same SNPs in separate trials. The frequency of differently present tags matched our predictions for the Drosophila genome, indicating that we are not selecting a biased subset of tags.

A feature of SNP detection by this method (and the related approach described, for instance, in Example 2) is that digestion of the genomic DNA with a specific restriction endonuclease creates one set of flanking tags and allows detection of a specific set of SNPs within the sequences cut by that restriction endonuclease. Digestion of the same DNA using a different restriction endonuclease will generate a separate set of flanking tags and thereby identify a different group of SNPs. If it is desired to discover or genotype additional SNPs, then increasing the number of digestions with different restriction endonucleases is expected to increase the number of SNPs found.

We tested this aspect of the system by separately digesting the genomic DNA prepared from the above analysis with XhoI, a 6-cutter restriction enzyme with a different recognition site sequence than EcoRI. This preparation detected a different set of SNPs, as shown by the different pattern of red, green and yellow spots on the array. Thus, the observed data closely match the predictions and suggest the isolation of genomic tags flanking restriction sites allows for the rapid discovery and genotyping of SNPs in the genome.

Example 2

Use of Extension from Mismatched Restriction Sites for SNP Discovery and Mapping This example provides methods for detecting polymorphism using extension from mismatched restriction sites. A schematic overview of the exemplary method is provided in FIG. 6.

Methods

Genomic DNA from two individual flies (referred to as individuals A and B) were separately extracted by using a Blood and cell culture DNA midi kit (Qiagen, Valencia, Calif.; cat#13343). The DNA was completely digested with the same 4, 5 or 6-cutter restriction enzymes (essentially as described above), then purified with a Qiaquick PCR purification kit (Qiagen, Valencia, Calif.; cat#28106).

10 µg of each of the digested and purified genomic DNA preparations (A and B) was mixed as a primer and template DNA mixture, and fluorescently labeled dCTP or dUTP and unlabeled dNTPs were mixed as a dNTPs resource. A routine PCR reaction was set up. If using Cy5-dCTP to label the reaction, an example of the reaction was set up in a 0.2 ml PCR tube as shown below:

| | |
|---|---|
| Genomic DNA A: | 30 µl |
| Genomic DNA B: | 30 µl |
| 10x PCR buffer: | 10 µl |
| 10 mM dATP, dTTP, dGTP: | 1 µl |
| 4 mM dCTP: | 1 µl |
| 1 mM cy5-dCTP: | 1 µl |
| Add dH$_2$O to 100 µl | 26 µl |

This was mixed and 1 units (1 units/µl) DNA taq polymerase added (though another DNA polymerase could be substituted). This was mixed again and the tube briefly spun in a microcentrifuge to keep all the mixture at the bottom of the tube. As a negative control, 20 µg genomic A or B alone (annealed to itself) was labeled as above; subtracting signal from this negative control allowed removal of noise and signals from, for instance, transposable elements.

The PCR reaction was carried out in a PCR machine with six cycles of 95° C. one minute and then 72° C. (or 68° C. for some special polymerases that prefer 68° C. as an extension temperature, for example HiTaq DNA polymerase from Invitrogen) for 60 minutes. The amplified and labeled reaction mixture was then purified with a Qiaquick PCR purification kit (Qiagen, Valencia, Calif.) and then resuspended in 4×SSC, 1.5 mg/ml polyA and 0.3% SDS solution.

The preparation was inserted in a boiling water bath for 2 minutes, and then cooled down for 30 seconds by a brief spinning in a microcentrifuge. The labeled cDNA mixture was then loaded onto a microarray slide, covered with a cover slip, put into a hybridization chamber, and hybridized in a 65° C. water bath for about 16 hours. After washing, the microarray slide was scanned with a Genepix 4000B scanner (Axon Instruments, now Molecular Devices, Union City, Calif.) and the data was analyzed.

Results

Figure 7:
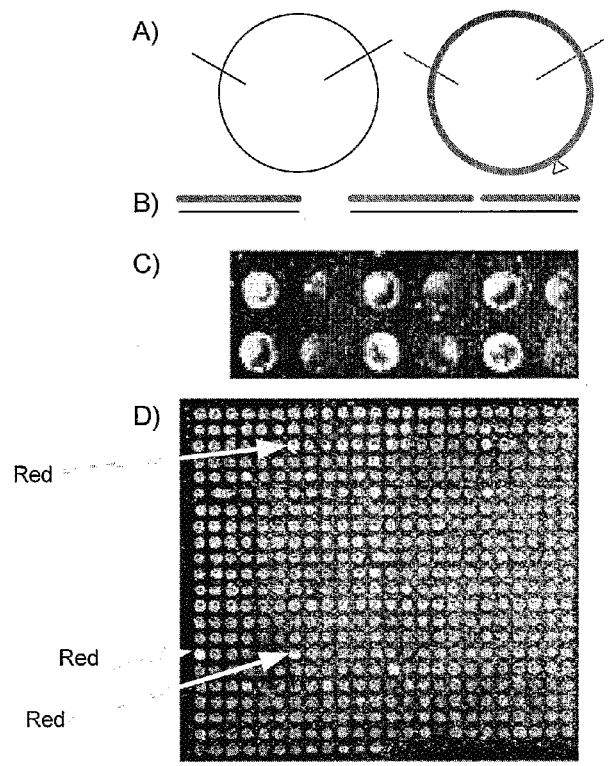
FIG. 7 illustrates testing and demonstration of an extension method for detection of polymorphisms.

A series of experiments was performed to test the application of this technique to SNP discovery. The approach relies on the specificity of primer extension at differently cut DNA in the annealed DNA populations. Background extension could result from non-specific shearing of the genomic DNA, hybridization of related sequences, or incomplete digestion of restriction sites. We first tested if SNPs in a restriction site can be detected by digestion, annealing, and extension in a simplified system. High specificity-labeling of DNA was found only at the region where two smaller fragments anneal to a larger fragment (see FIG. 7).

Because the technique worked in the simple setting tested above, a test hybridization using FRT 82 and rucuca genomic DNA annealed after BamHI digestion was also performed. Labeled material was hybridized to a microarray made up of overlapping 3 kb clones of Drosophila genomic DNA. One high-intensity spot out of every 30 was observed, similar to what would be expected given the rate of polymorphisms in the Drosophila genome. The rate of background, artifactual extension and hybridization was assayed in the context of the full genome by annealing FRT 82 genomic DNA cut with BAMHI to itself. We saw strong hybridization to only a few array elements, indicating that sources of artifactual hybridization are not prevalent in this technique.

This approach has also been used to map a recombination breakpoint. Genomic DNA fragments created and labeled as above from a fly line that contains a $3^{rd}$ chromosome with a mixture of FRT 82 and rucuca chromosomal material was annealed to similarly labeled genomic DNA fragments from each of the parental chromosomes in two different reactions. In chromosomal regions where the recombinant line genome matches the parental line, no extension or subsequent hybridization is predicted, since the restriction site pattern is the same. In chromosomal regions where the recombinant DNA comes from the other parent, the annealed DNA is predicted to produce extension products from differently present restriction sites which would then be detected by hybridization to the array.

Figure 8:
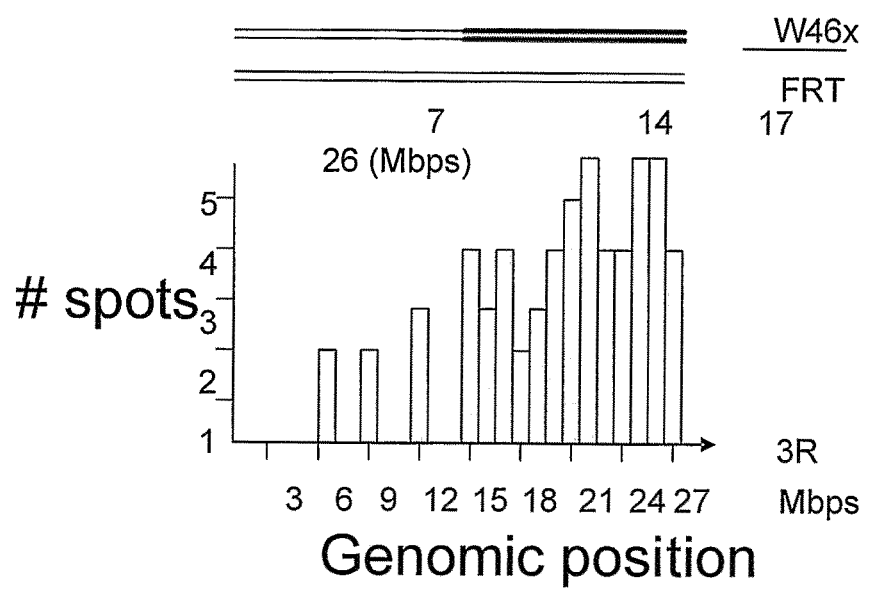
FIG. 8 illustrates mapping of a recombination breakpoint. Genomic DNA from a recombinant line (thick portion of the line is rucuca DNA, thin is FRT 82 DNA) was annealed to FRT 82 parental DNA after digestion. Extension from mismatched cut sites results in strong labeling of spots after position 14,600,000. Labeling observed to the left of this position is at known repetitive DNA that is labeled in all experiments.

This in fact was observed (FIG. 8). In one reaction, the high-intensity spots mapped to the left half of chromosome 3, and only a few spots mapped to the right side. In the other reaction, high-intensity spots mapped to the right side. The pattern of hybridization switched modes (from high-intensity spots being present to none, and vice versa) near genomic position 14,600,000 of the $3^{rd}$ chromosome. This suggests that the recombinant line had a recombination event in this region. Thus, the presence and absence of restriction sites in the recombinant line compared to each parental line, as assayed on a microarray, provides a rapid method to identify a small chromosomal region of interest.

This disclosure provides various methods for detection of polymorphisms, including particularly the detection of SNPs and other polymorphisms in characterized and uncharacterized genomes. The disclosure further provides arrays of tags useful in detection of polymorphisms. It will be apparent that the precise details of the methods described may be varied or modified without departing from the spirit of the described invention. We claim all such modifications and variations that fall within the scope and spirit of the claims below.

We claim:

1. A method of isolating fragment tags from genomic DNA, the method comprising:
   (a) shearing a preparation of genomic DNA to fragments about 3-5 kb in length; and
   (b) digesting the preparation of genomic DNA with a restriction enzyme;
   wherein (a) and (b) can occur in either order or concurrently and wherein (a) and (b) produce a collection of DNA fragments comprising at least some DNA fragments comprising a restriction site at one end and which are blunt at the other end; and
   (c) isolating DNA fragments about 1 kb in length from the collection of DNA fragments, which DNA fragments are the fragment tags.

2. The method of claim 1, comprising:
   shearing genomic DNA to fragments about 3-5 kb in length to produce sheared DNA fragments;
   filling in any resultant overhanging ends on the sheared DNA fragments;
   digesting the sheared DNA fragments with a restriction enzyme, to produce a collection of DNA fragments at least some of which have a restriction site at one end and a blunt end on the other end;
   isolating DNA fragments about 1 kb in length from the collection of DNA fragments;
   ligating a linker to the isolated DNA fragments about 1 kb in length at the restriction site to produce linkered DNA fragments;
   isolating the linkered DNA fragments; and
   recovering the DNA fragments by digesting away the linker, wherein the DNA fragments are the fragment tags.

3. The method of claim 1, further comprising ligating a linker to the isolated DNA fragment tags.

4. A method of isolating fragment tags from genomic DNA comprising:
   digesting genomic DNA with a restriction enzyme to produce digested DNA fragments;
   ligating a linker to the digested DNA fragments at the restriction site to produce linkered DNA fragments;
   isolating the linkered DNA fragments;
   shearing the linkered DNA fragments to about 1 kb in length to produce a collection of DNA fragments, at least some of which have a linkered restriction site at one end and a blunt end at the other end;
   filling in any resultant overhanging ends on the collection of DNA fragments; and
   isolating DNA fragments about 1 kb in length from the collection of DNA fragments, wherein the isolated DNA fragments are the fragment tags.

5. The method of claim 4, further comprising recovering the DNA fragments by digesting away the linker.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
tttcgacgct cgcatctgga cagg                                           24

<210> SEQ ID NO 2
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 2
aattcctgtc cagatgcgag cgtcg                                          25

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ctgctcgaat tcaagcttct                                                20

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 4
tcgagctgtc cagatgcgag cgtcg                                          25
```